United States Patent
Hatta et al.

(10) Patent No.: US 10,959,749 B2
(45) Date of Patent: Mar. 30, 2021

(54) MEDICAL DEVICE AND TREATMENT METHOD

(71) Applicant: TERUMO KABUSHIKI KAISHA, Tokyo (JP)

(72) Inventors: Tomonori Hatta, Cupertino, CA (US); Junichi Kobayashi, Cupertino, CA (US); Taiga Nakano, Sunnyvale, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 42 days.

(21) Appl. No.: 15/377,131

(22) Filed: Dec. 13, 2016

(65) Prior Publication Data

US 2017/0238960 A1    Aug. 24, 2017

Related U.S. Application Data

(63) Continuation of application No. PCT/JP2015/066945, filed on Jun. 11, 2015.

(Continued)

(51) Int. Cl.
*A61B 17/3207* (2006.01)
*A61B 17/221* (2006.01)
(Continued)

(52) U.S. Cl.
CPC .... *A61B 17/320725* (2013.01); *A61B 17/221* (2013.01); *A61B 17/320758* (2013.01);
(Continued)

(58) Field of Classification Search
CPC .... A61B 17/320725; A61B 17/320758; A61B 17/3207; A61B 2017/00539;
(Continued)

(56) References Cited

U.S. PATENT DOCUMENTS 5,501,694 A * 3/1996 Ressemann .... A61B 17/320725
604/22
5,899,915 A   5/1999 Saadat
(Continued)

FOREIGN PATENT DOCUMENTS

JP   2001-087275 A   4/2001
JP   2001-524844 A   12/2001
(Continued)

OTHER PUBLICATIONS

International Search Report (PCT/ISA/210) dated Oct. 6, 2015, by the Japanese Patent Office as the International Searching Authority for International Application No. PCT/JP2015/066945.
(Continued)

*Primary Examiner* — Jocelin C Tanner
(74) *Attorney, Agent, or Firm* — Buchanan Ingersoll & Rooney PC

(57) ABSTRACT

A medical device for removing a stenosis of a living body lumen includes a drive shaft configured to be driven by an operation at a proximal side thereof and including a treatment member disposed at a distal side thereof, a housing configured to accommodate the proximal side of the drive shaft therein, and a holding member configured to suppress unnecessary movement of the drive shaft. A proximal end of the holding member is fixed to the housing, and an inner surface of the holding member and an outer surface of the drive shaft are slidable relative to one another.

26 Claims, 24 Drawing Sheets

Related U.S. Application Data

(60) Provisional application No. 62/011,860, filed on Jun. 13, 2014, provisional application No. 62/011,874, filed on Jun. 13, 2014, provisional application No. 62/011,883, filed on Jun. 13, 2014, provisional application No. 62/012,576, filed on Jun. 16, 2014.

(51) Int. Cl.
*A61B 17/32* (2006.01)
*A61B 17/00* (2006.01)
*A61B 17/22* (2006.01)

(52) U.S. Cl.
CPC ............... *A61B 2017/00867* (2013.01); *A61B 2017/00991* (2013.01); *A61B 2017/22002* (2013.01); *A61B 2017/2212* (2013.01); *A61B 2017/320004* (2013.01); *A61B 2017/320716* (2013.01); *A61B 2017/320766* (2013.01)

(58) Field of Classification Search
CPC ........... A61B 2017/22001; A61B 2017/22038; A61B 2017/22079; A61B 2017/22082; A61B 2017/320716; A61B 2017/320733; A61B 2017/320775; A61F 2/013; A61F 2002/016; A61M 25/09041
See application file for complete search history.

(56) References Cited

U.S. PATENT DOCUMENTS

| | | | | |
|---|---|---|---|---|
| 6,143,009 | A | * | 11/2000 | Shiber ............ A61B 17/320758 606/159 |
| 6,454,775 | B1 | * | 9/2002 | Demarais ....... A61B 17/320725 606/128 |
| 2001/0031981 | A1 | * | 10/2001 | Evans .................. A61B 17/221 606/200 |
| 2002/0058956 | A1 | | 5/2002 | Honeycutt et al. |
| 2008/0097487 | A1 | * | 4/2008 | Pool ........................ A61F 5/003 606/151 |
| 2009/0069829 | A1 | * | 3/2009 | Shturman ...... A61B 17/320725 606/159 |
| 2012/0239064 | A1 | * | 9/2012 | Cartier ................. A61B 17/221 606/159 |
| 2013/0046316 | A1 | | 2/2013 | Sullivan et al. |

FOREIGN PATENT DOCUMENTS

WO        WO 98/24373 A1    6/1998
WO        WO 00/51503 A1    9/2000

OTHER PUBLICATIONS

Written Opinion (PCT/ISA/237) dated Oct. 6, 2015, by the Japanese Patent Office as the International Searching Authority for International Application No. PCT/JP2015/066945.

* cited by examiner

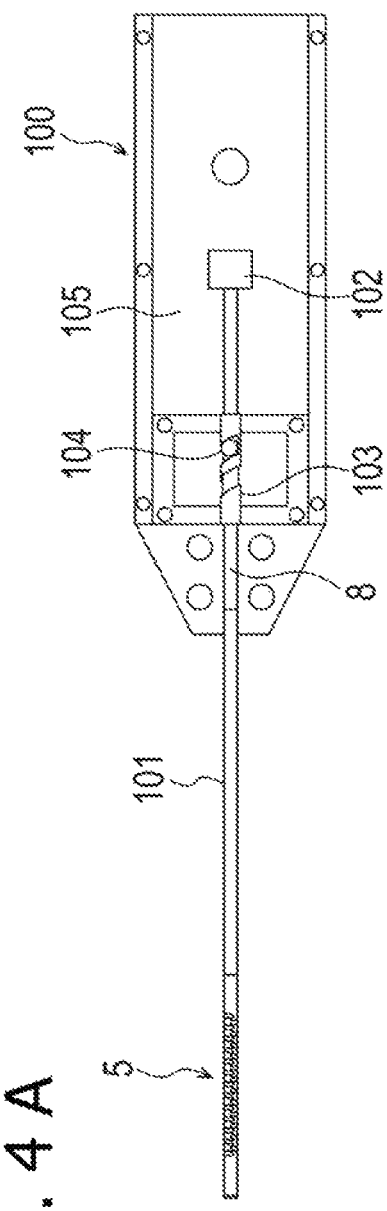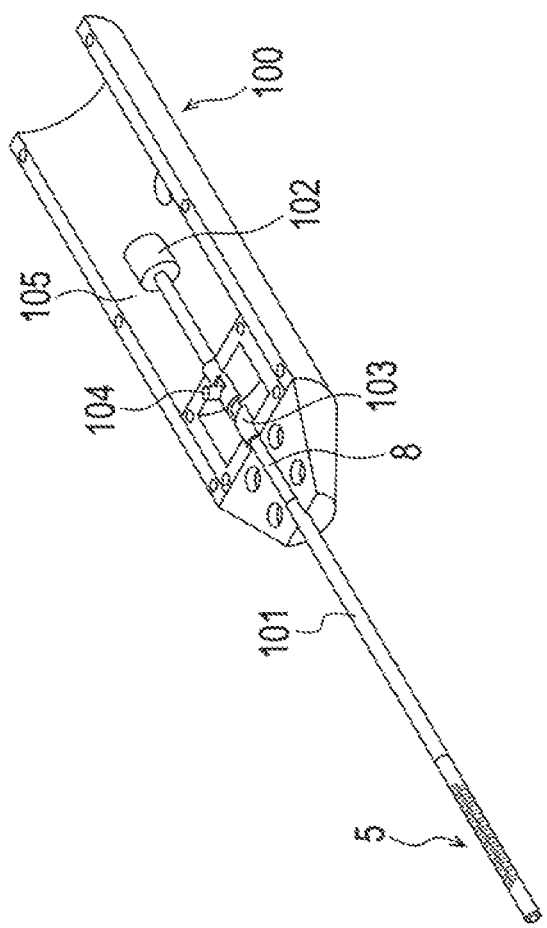
FIG. 4A
FIG. 4B

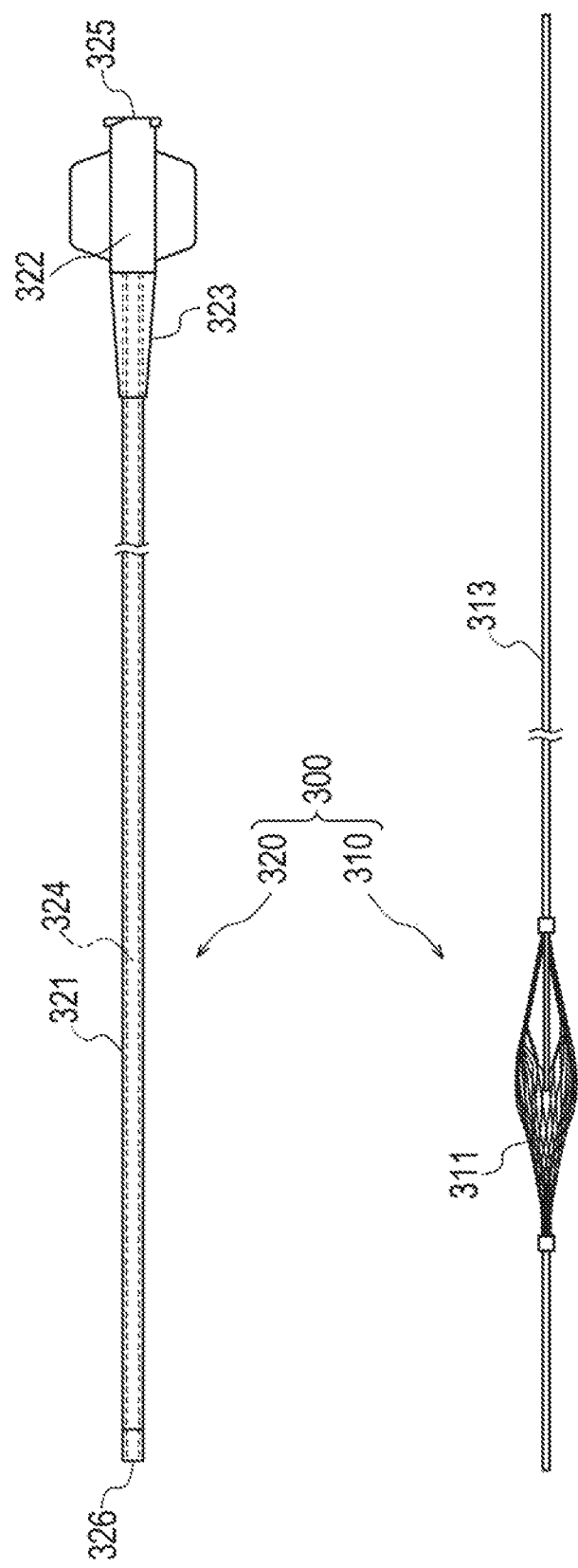

DISTAL END →

← DISTAL END

DISTAL END →

← DISTAL END

MEDICAL DEVICE AND TREATMENT METHOD

CROSS-REFERENCES TO RELATED APPLICATIONS

This application is a continuation of International Application No. PCT/JP2015/066945 filed on Jun. 11, 2015, and claims priority to U.S. Provisional Application No. 62/011,860 filed on Jun. 13, 2014, U.S. Provisional Application No. 62/011,874 filed on Jun. 13, 2014, U.S. Provisional Application No. 62/011,883 filed on Jun. 13, 2014 and U.S. Provisional Application No. 62/012,576 filed on Jun. 16, 2014, the entire content of all five of which is incorporated herein by reference.

TECHNICAL FIELD

The present disclosure generally relates to a medical device and a method for treating a stenosis or an occluded portion of a living body lumen. More specifically, the present disclosure relates to a medical device and a treatment method for removing a plaque (or a thrombus) from a living body lumen such as an artery or a vein.

BACKGROUND DISCUSSION

Atherosclerosis is caused by fatty acid precipitated on the lower side of an intimal layer of a blood vessel. At an initial state, comparatively soft fatty acid is precipitated on the lower side of an intimal layer. As time passes, cholesterol composition is captured into the precipitated fatty acid thereby to form a calcified atheroma layer. The inside of the blood vessel becomes a constricted state or a state in which the inside of the blood vessel is occluded with the formed atheroma layer. By virtue of this, the blood flow is inhibited. If this state is left as it is, then in the case of the heart, an angina pectoris or a myocardial infarction is developed, and in the case of a limb, a necrosis of a finger of a hand and a leg or intermittent claudication is developed.

In atherectomy surgery, treatment involving removal of a grown arteriosclerosis layer from a blood vessel is performed through a catheter. Usually, atherectomy surgery by itself is not performed, but rather atherectomy surgery is performed in combination with balloon angioplasty. In order to remove an arteriosclerosis layer and maintain a lumen opened by angioplasty, stent indwelling is performed. It has been pointed out in many study reports that, even if treatment is performed, a new arteriosclerosis layer can grow in the inside of the stent. In this case, atherectomy surgery, balloon angioplasty and stent indwelling are performed frequently. In recent years, investigations are performed for reducing the stenosis rate by a drug releasing stent which is expected to have an effect against hypertrophic atheroma.

Atherectomy surgery can be utilized for treatment of chronic occlusion which obstructs the blood flow fully. In several examples, as the blood flow rate decreases, the intimal layer of the blood vessel gradually grows large. Various technologies for treating those diseases have been disclosed.

A thrombus is another factor which causes vascular occlusion. In several examples, a thrombus is generated when blood flow in a blood vessel bleeds to the circumference and is deposited there. The surface of an atheroma layer is susceptible to damage. Therefore, if the surface of an atheroma layer is damaged for some reason, then platelets in the circulating blood flow coagulate and form a thrombus. As a result, the blood vessel is occluded. In several examples, a thrombus exists together with an atheroma layer. A technology for removing a deposited thrombus using a balloon has been used for a long period of time.

Even if atherectomy surgery is carried out, an atheroma may not be removed in some cases due to the location, size and hardness. In such a case, an influence is had on stent indwelling or some other treatment. The medical device disclosed here is able to remove an substance in a blood vessel such as an artery or a vein, namely, an occluding substance which constricts or occludes a vascular lumen.

SUMMARY

An embodiment of the present disclosure is a medical device for removing a stenosis of a living body lumen, including a drive shaft configured to be driven by an operation at a proximal side thereof and including a treatment member disposed at a distal side thereof, a housing configured to accommodate the proximal side of the drive shaft therein, and a holding member configured to suppress unnecessary movement of the drive shaft. A proximal end of the holding member is fixed to the housing, and an inner surface of the holding member and an outer surface of the drive shaft are slidable relative to one another.

Another embodiment of the present disclosure is a treatment method for treating a stenosis of a living body lumen, including providing an elongate body including an expandable member at a distal end portion thereof, inserting the elongate body into the living body lumen and advancing the expandable member toward the stenosis, expanding the expandable member in order to contact the expandable member with the stenosis, successively moving the expandable member in one rotational direction and an opposite rotational direction to remove the stenosis, and pulling out the elongate body from the living body lumen.

A further embodiment of the present disclosure is a treatment method for treating a stenosis of a living body lumen, including providing an elongate body including an expandable member at a distal end portion thereof, inserting the elongate body into the living body lumen and advancing the expandable member toward the stenosis, expanding the expandable member in order to contact the expandable member with the stenosis, moving the expandable member such that at least part of the expandable member passes along a spiral locus to remove the stenosis, and pulling out the elongate body from the living body lumen.

BRIEF DESCRIPTION OF THE DRAWINGS

FIG. 4A is a schematic view depicting a motor unit of the catheter system, and FIG. 4B is a perspective view of the motor unit depicted in FIG. 4A.

FIG. 6 is a schematic view depicting a filter device.

DETAILED DESCRIPTION

Figure 1:
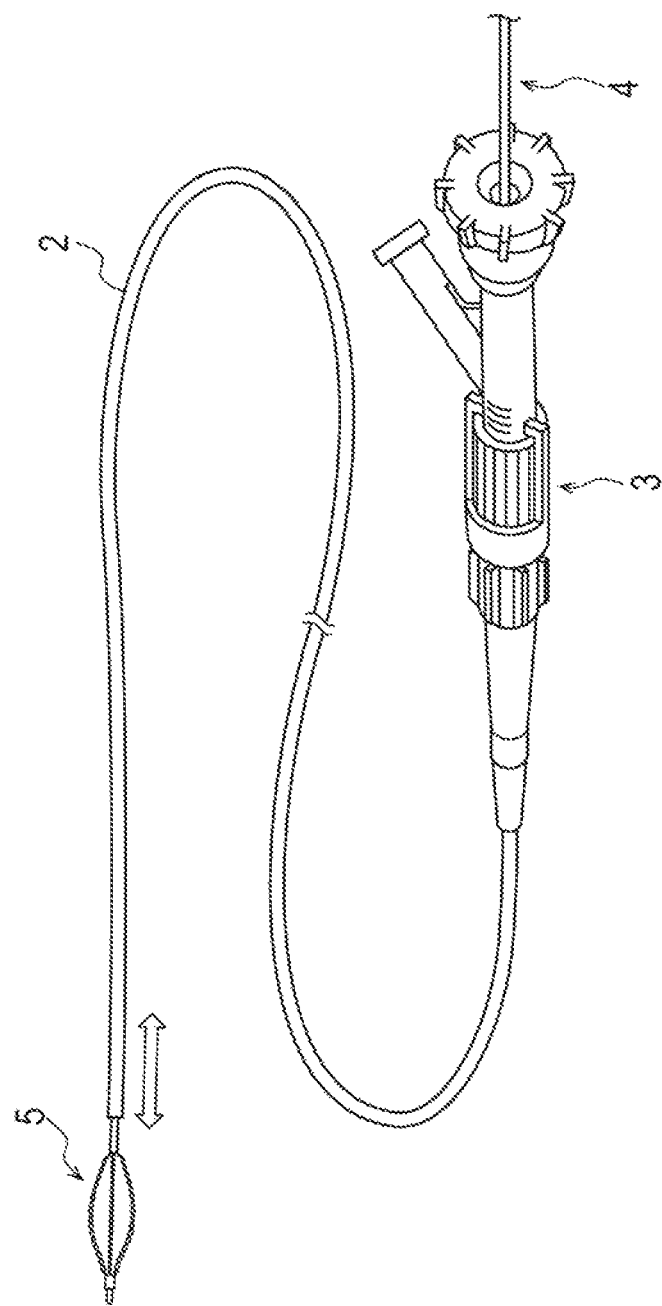
FIG. 1 is a schematic view depicting a catheter system which is an embodiment of a medical device used to perform treatment.

In the following, atherectomy devices to which the disclosed technology is applied are described in detail based on embodiments with reference to the accompanying drawings. These embodiments represent examples of the inventive atherectomy device disclosed here. Dimensional ratios in the drawings are exaggerated for the convenience of illustration and are sometimes different from actual ratios.

In the embodiments of the atherectomy device described below, an example is described in which an atherectomy device is applied to a catheter system for removing an occluding substance which constricts or occludes a vascular lumen.

First Embodiment

Figure 2:
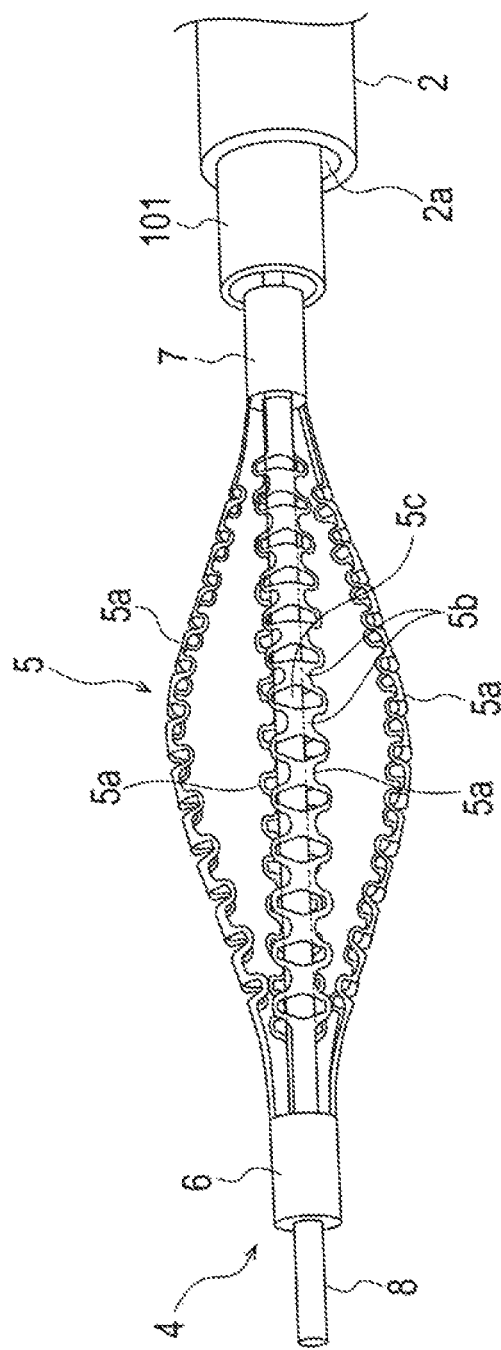
FIG. 2 is a schematic view depicting a form of a removing member depicted in FIG. 1.
Figure 3:
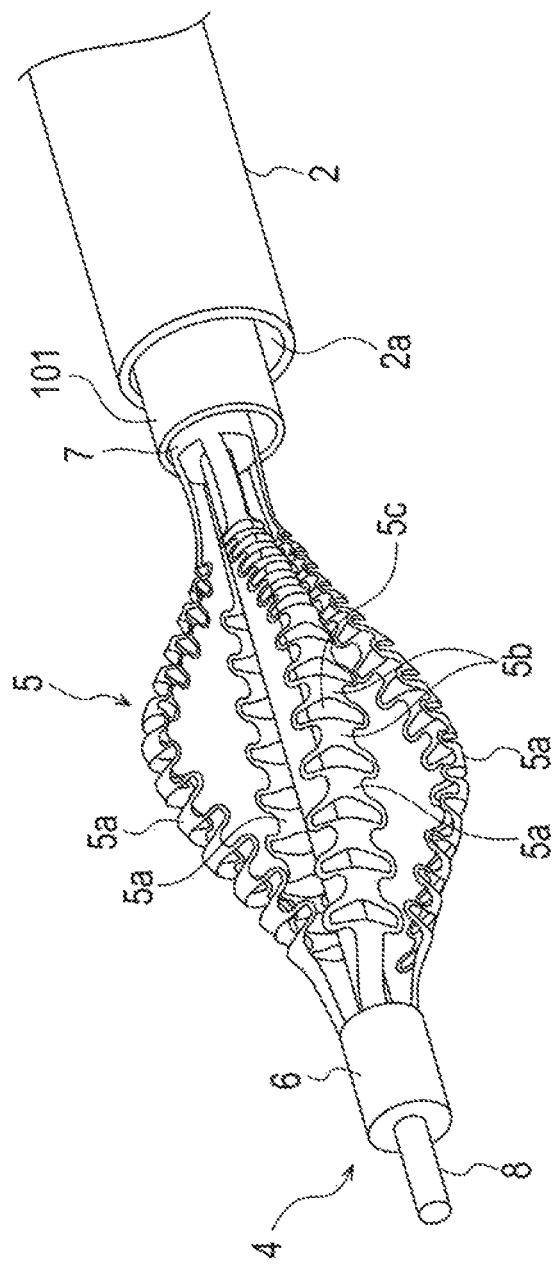
FIG. 3 is a perspective view of the removing member depicted in FIG. 2.
Figure 7:
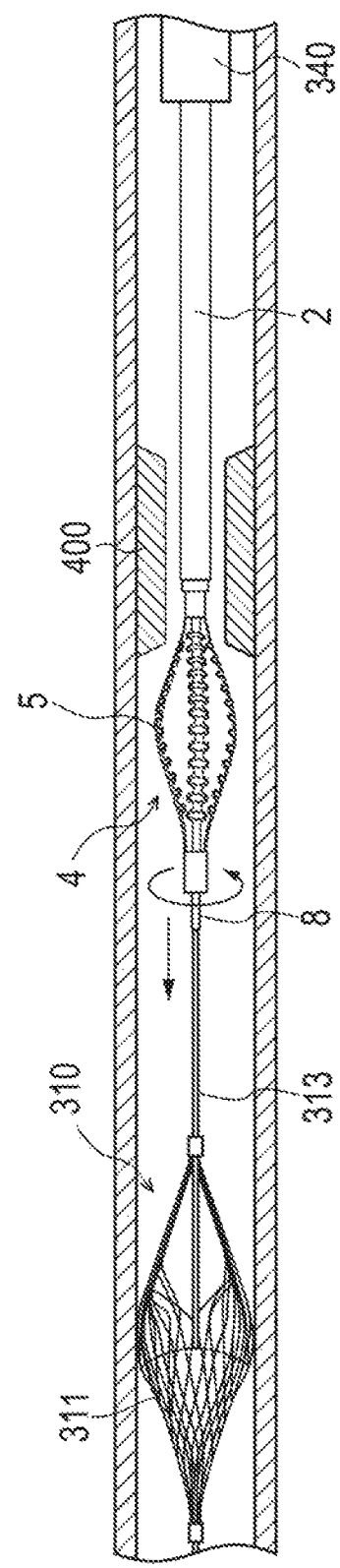
FIG. 7 is a diagrammatic view illustrating a manner in which the filter device depicted in FIG. 6 is used in a living body lumen.
Figure 8:
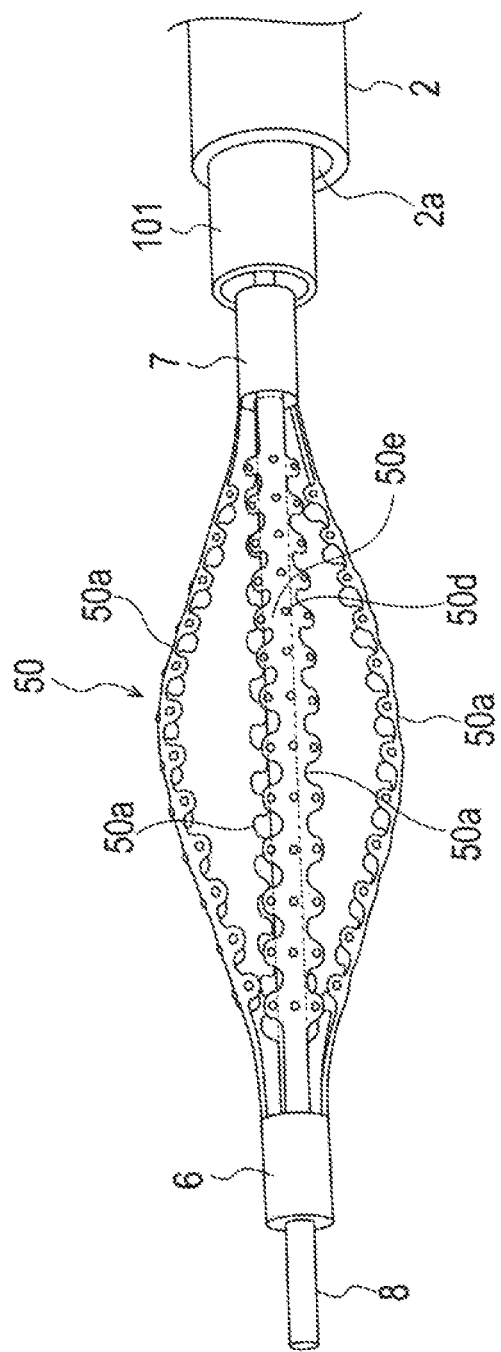
FIG. 8 is a schematic view depicting a different form of the removing member depicted in FIG. 1.
Figure 9:
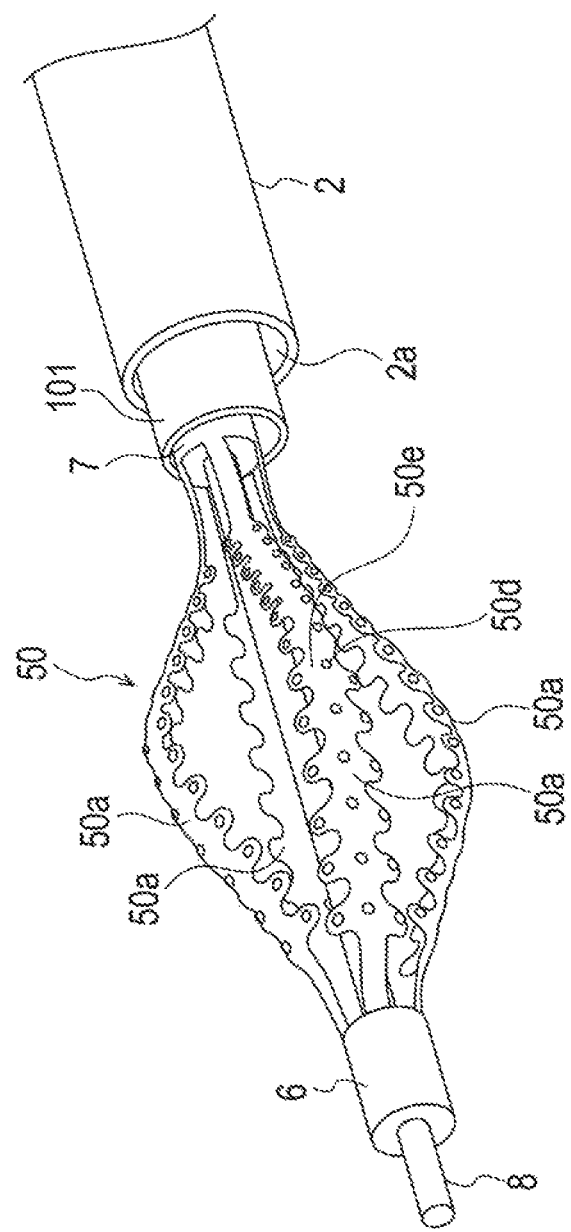
FIG. 9 is a perspective view of the removing member depicted in FIG. 8.
Figure 10:
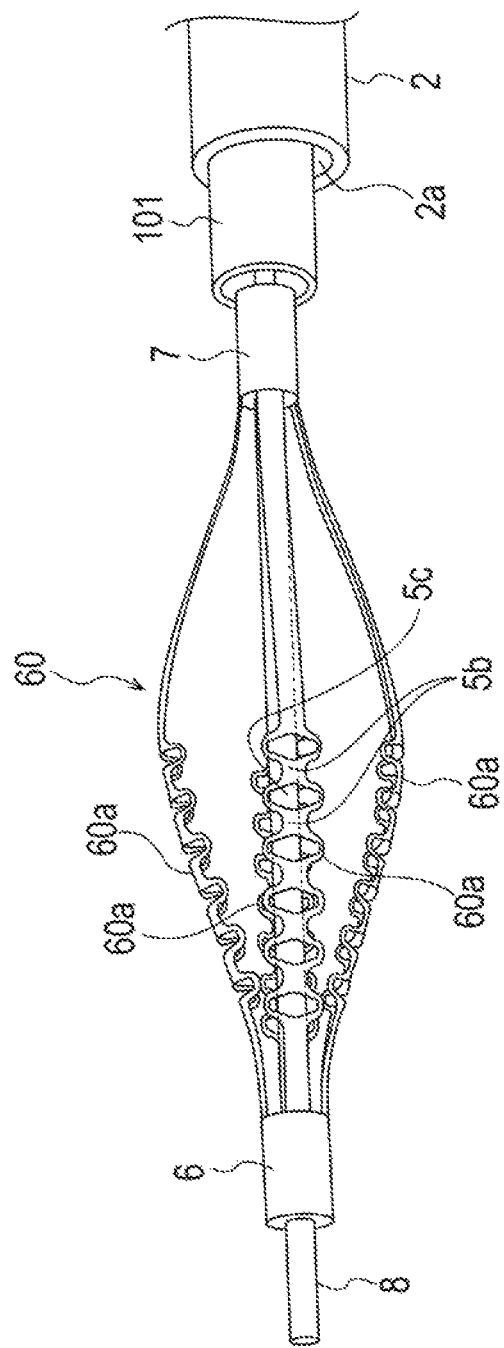
FIG. 10 is a schematic view depicting a modification to the removing member depicted in FIG. 1.
Figure 11:
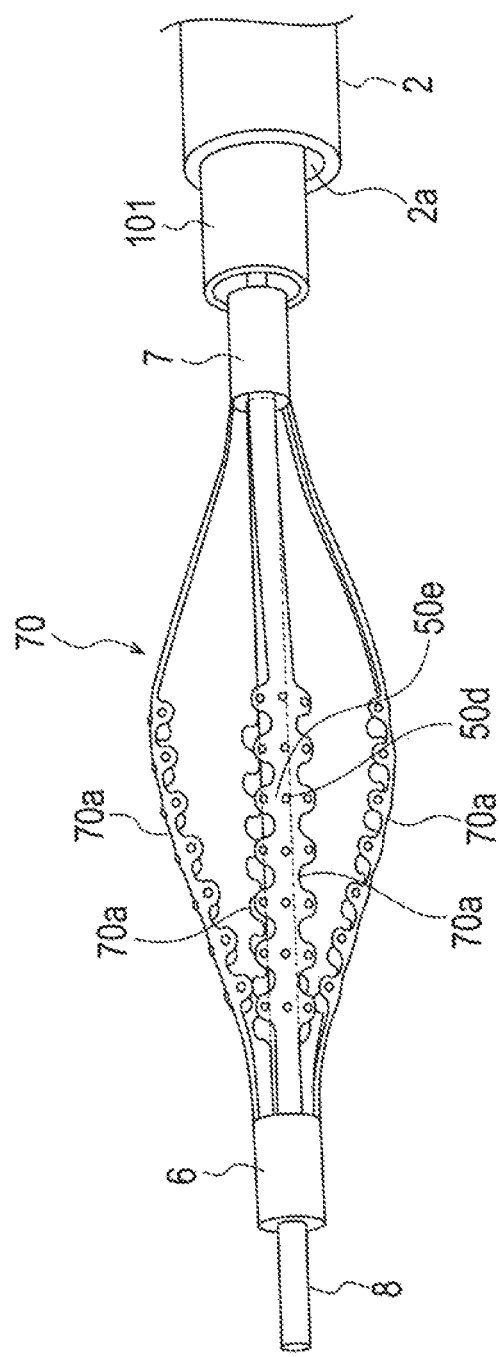
FIG. 11 is a schematic view depicting a modification to the removing member depicted in FIGS. 8 and 9.
Figure 12:
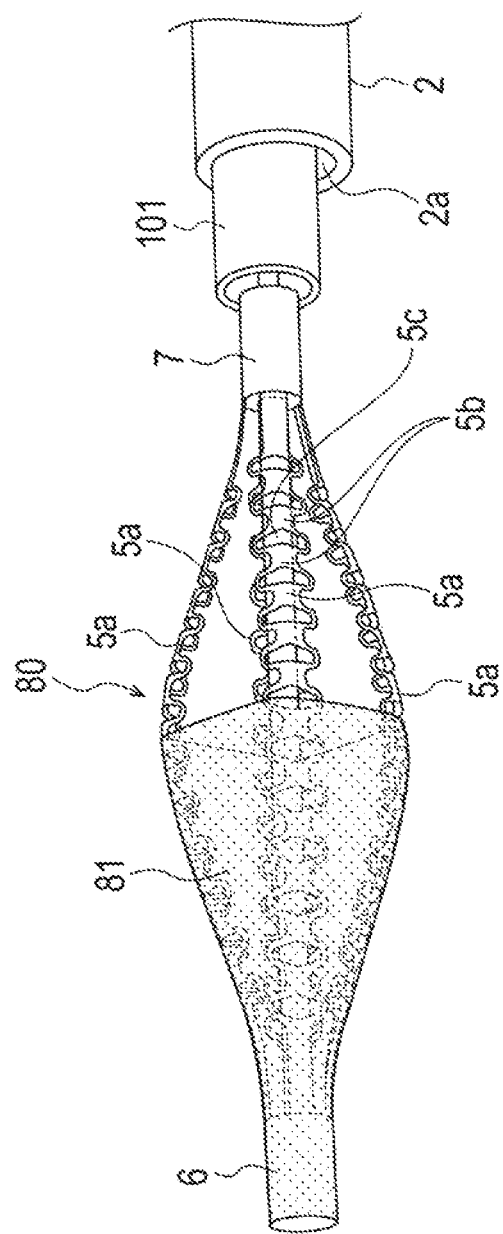
FIG. 12 is a schematic view depicting a modification to the removing member depicted in FIG. 10.
Figure 13:
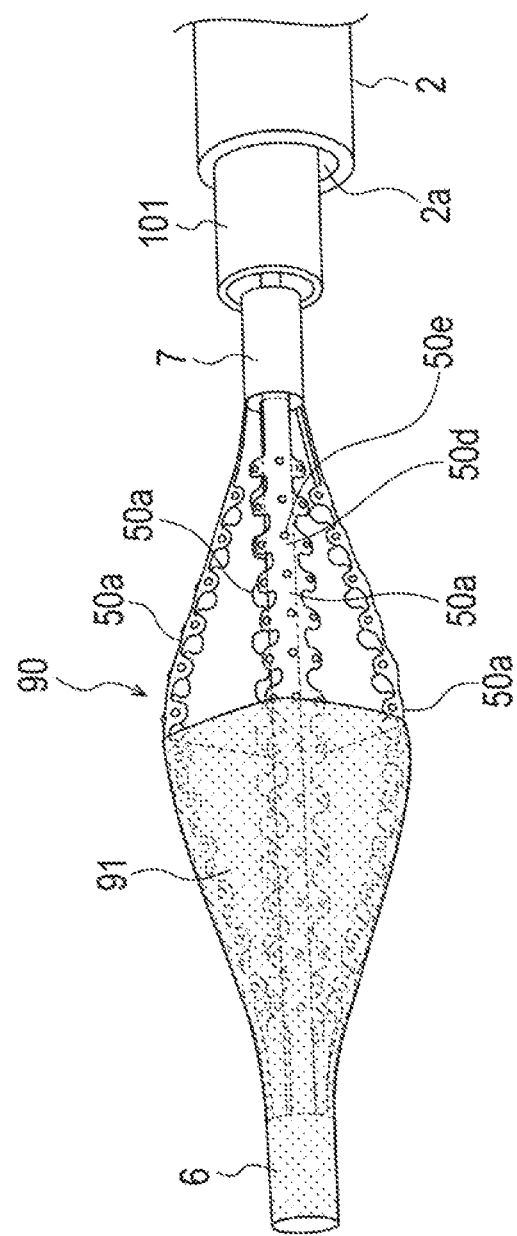
FIG. 13 is a schematic view depicting a modification to the removing member depicted in FIG. 11.

FIG. 1 is a lateral view depicting an embodiment of a catheter system 1, FIG. 2 is a lateral view of a removing member 5 of a removing device 4 depicted in FIG. 1, and FIG. 3 is a perspective view of the removing member 5 depicted in FIG. 2. FIG. 4A is a sectional view of a proximal side or proximal end of the catheter system 1 depicted in FIG. 1, and FIG. 4B is a perspective view of FIG. 4A. FIGS. 5A to 5D are diagrammatic views when the removing member 5 acts in a stenosis 400. FIG. 6 is a lateral view depicting a filter device 300 according to the embodiment. FIG. 7 is a diagrammatic view illustrating an example of use of the filter device 300. FIG. 8 is a lateral view of a removing member 50 as a different from of the removing member 5 of the removing device 4 depicted in FIG. 1, and FIG. 9 is a perspective view of the removing member 50 depicted in FIG. 8. FIG. 10 is a view depicting a modification to the removing member 5 depicted in FIGS. 2 and 3. FIG. 11 is a view depicting a modification to the removing member 50 depicted in FIGS. 8 and 9. FIG. 12 is a view depicting a modification to the removing member 60 depicted in FIG. 10. FIG. 13 is a view depicting a modification to the removing member 70 depicted in FIG. 11.

For the convenience of description, an end of the catheter system 1 at the side to be inserted into a living body (at the left side in FIGS. 1 to 9) is referred to as the "distal end" (or remote position end), and an end of the catheter system 1 at the side at which a hub 3 is disposed (at the right side in FIGS. 1 to 9) is referred to as the "proximal end" (or near position end). This similarly applies also to the other embodiments hereinafter described.

The catheter systems depicted in the figures are medical devices for removing blockage or obstruction in a blood vessel such as an artery or a vein, namely, an occluding substance which constricts or occludes the vascular lumen to assure blood flow.

As depicted in FIG. 1, the catheter system 1 includes an outer catheter or outer sheath 2, a hub 3 provided at a proximal end portion of the outer catheter 2, a removing device 4 inserted or positioned in the outer catheter 2 for rotation around an axis and for movement in an axial direction with respect to the outer catheter 2, and a removing member 5 (expandable member) disposed on the distal side or distal end of the removing device 4 and configured to drill and remove an occluding substance which constricts or occludes (blocks or obstructs) a vascular lumen. The occluding substance includes not only a substance which occludes a vascular lumen but also various substances which constrict (partially occlude) the lumen even if they do not fully occlude the lumen. In particular, examples of the occluding substances include thrombi, fatty streaks, plaques, calcified lesions, intimal hypertrophy of a vessel, arteriosclerosis layers and so forth.

As depicted in FIG. 1, the outer catheter 2 has an outer surface which is smooth from the proximal side (proximal end) to the distal side (distal end) and has a cylindrical shape having a lumen on the inner side thereof such that the removing device 4 can be inserted into the lumen in the outer catheter 2. The outer catheter 2 has flexibility such that, when it is inserted into a blood vessel, the outer catheter 2 can trace or follow the curve of the blood vessel.

Examples of the constituent material for forming the outer catheter 2 include polyolefin such as polyethylene, polypropylene or polybutadiene, polyvinylchloride, polyurethane, polyether polyurethane, ethylene-vinyl acetate copolymer, polyethylene terephthalate, polybutylene terephthalate, polyamide, polyether polyamide, polyester polyamide, various thermoplastic elastomers such as styrene-based, polyolefin-based, polyurethane-based, polyester-based, polyamide-based, polybutadiene-based, trans-polyisoprene-based, fluorinated rubber-based and chlorinated polyethylene-based elastomers and so forth. Further, blends of two or more of the materials mentioned or layers of two or more of the materials may be used.

Preferably, such an outer catheter 2 as described above has an enhanced X-ray contrast property at least at the distal end of the outer catheter 2 such that the outer catheter or portion of the outer catheter can be visually recognized, upon removal of an occluding substance in a blood vessel, under X-ray fluoroscopy. In this case, for example, an X-ray opaque material such as barium sulfate, platinum, gold or tungsten may be blended in the constituent material at least of the outer catheter 2 or an X-ray contrast marker constituted from the X-ray opaque material described hereinabove may be provided. In the present embodiment, an X-ray contrast marker is provided on the distal end of the outer catheter 2.

As depicted in FIGS. 2 and 3, the removing member 5 for removing an occluding substance generated in a blood vessel is fixed to a distal end portion of the removing device 4.

The removing member 5 is configured for deformation, by an operation performed for moving the outer catheter 2 in directions indicated by a double-sided arrow in FIG. 1, between a state in which the removing member 5 is accommodated in the outer catheter 2 (the removing member 5 is covered by the outer catheter) and has a reduced diameter and an expanded state in which the removing member 5 projects from or distally beyond a distal end opening 2a of the outer catheter 2 and is expanded in a radial direction by the elastic restoring force of the removing member 5 itself as depicted in FIGS. 2 and 3. The removing member 5 is shaped such that it exhibits the expanded state when it is in a natural state (state in which it is not acted upon by any external force). When an occluding substance (occlusion) is to be removed by the removing member 5, the removing member 5 is positioned to project from the distal end opening 2a of the outer catheter 2 and treatment for removing the occluding substance (occlusion) is performed in the expanded state of the removing member 5.

The following describes the removing member 5 when it exhibits the expanded state (i.e., when the removing member 5 is in the expanded state).

As depicted in FIGS. 2 and 3, the removing member 5 is configured from four relatively narrow struts 5a each in the form of a thin board connected to a distal end part 6 (distal end piece) and a proximal end part 7 (proximal end piece). A drive shaft 8 (elongated member) extends in an internal space of the removing member 5. The drive shaft 8 has a guide wire lumen which is open from the distal end to the proximal end of the removing device 4 and into which a guide wire can be inserted. The distal end part 6 and the proximal end part 7 are fixed to the drive shaft 8, and if a rotational force is transmitted from the proximal end of the removing device 4, then the drive shaft 8 is rotated to allow rotation of the removing member 5 connected to the distal end part 6 and the proximal end part 7.

The distal end part 6 can be disposed for sliding movement on the drive shaft 8, for example, by not fixing the distal end part 6 to the drive shaft 8. Consequently, if the removing member 5 in the expanded state is inserted into a stenosis, the removing member 5 is acted upon by reactive force from the stenosis, and when the distal end part 6 slidably moves on the drive shaft 8, the removing member 5 can be reduced in diameter. However, if it is intended to transmit rotational force of the drive shaft 8 to the distal end, then the distal end part 6 may be fixed to the drive shaft 8 while the proximal end part 7 is placed into a state in which it is not fixed to the drive shaft 8. Consequently, the proximal end part 7 is allowed to slidably move on the drive shaft 8.

As depicted in FIGS. 2 and 3, the struts 5a of the removing member 5 extend axially between the two parts 6, 7 and are disposed in a spaced relationship by 90 degrees from each other in a circumferential direction. In this embodiment illustrated by way of example, there are thus four circumferentially spaced-apart struts 5a arranged at 90 degree intervals. Further, a plurality of protrusions are formed on each strut 5a such that they project in a circumferential direction, and a plurality of substantially diamond-shaped holes 5c are formed at a thin board portion of the strut 5a sandwiched by the protrusions. Adjacent protrusions are connected by a connection area 5b so that a connection area 5b is located between adjacent protrusions and adjacent holes 5c.

As the constituent material of the removing member 5, for example, a shape-memory alloy is preferably used. As the shape-memory alloy, for example, Ni—Ti-based alloys such as Ni—Ti and Ni—Ti—Cu, Cu-based alloys such as Cu—Al—Mn and Cu—Al—Ni, Fe-based alloys such as Fe—Mn—Si, Au—Cd, Ag—Cd-based alloys, and ferromagnetic shape memory alloys such as Ni—Mn—Ga and Fe—Pd can be listed.

Now, an example of a method of use of the catheter system 1 is described. When treatment for removing an occluding substance in a blood vessel is to be performed, the removing device 4 having the removing member 5 disposed at the distal end of the removing device 4 is inserted into the outer catheter 2 until the removing member 5 is accommodated in a reduced diameter state in the inside at the distal end portion of the outer catheter 2. Then, the removing device 4 and the outer catheter 2 are inserted into a blood vessel and advanced to a target region in the blood vessel by operating the guide wire inserted in the guide wire lumen of the drive shaft 8. The situation then is monitored by X-ray contrast or the like.

Then, the removing device 4 disposed in the outer catheter 2 is advanced to the peripheral side (distal direction) in the blood vessel in a state in which the outer catheter 2 is fixed, at the proximal end of the outer catheter 2, so as not to move. Consequently, as depicted in FIGS. 2 and 3, the removing member 5 projects from the distal end opening 2a of the outer catheter 2 and is expanded in a radial direction into an expanded state by the elastic restoring force of the removing member 5 itself. Alternatively, the removing member 5 may be moved to the position shown in FIGS. 1-3 in which the removing member 5 projects beyond the distal end opening 2a of the outer catheter 2 by pulling back the outer catheter 2 in a state in which the removing device 4 is fixed at the hand side which may be held by the user.

Then, the removing member 5 is brought into contact with the occluding place in the blood vessel (i.e., the place of occlusion in the blood vessel), and the removing member 5 is rotated around the drive shaft 8. Consequently, the removing member 5 is rotated around the drive shaft 8 and the struts 5a grind the occluding substance which constricts or occludes the blood vessel.

Then, the removing member 5 is moved in the axially forward and rearward directions to perform removal of the occluding substance until the inner diameter of the blood vessel at the lesion affected area or occluded place reaches a target expansion rate (stenosis rate). At this time, since the removing member 5 is shaped such that it self-expands in a radial direction, it can normally apply pressing force equal to or higher than a predetermined level to the stenosis, and therefore, treatment can be performed without depending upon the position, magnitude and hardness of the stenosis.

Next, the action or operation of a motor unit 100 which drives the removing member 5 (drive shaft 8) is described with reference to a diagrammatic view depicted in FIG. 4A. The motor unit 100 is a box-type unit device having a space in the inside of the device. The distal end portion of the device has a lumen into which the drive shaft 8 is inserted or positioned, and has a reinforcing tube 101 whose proximal end is fixed to the motor unit 100. That is, the motor unit 100 includes a housing, and the proximal end portion of the reinforcing tube 101 is fixed to the housing of the motor unit 100. The drive shaft 8 is inserted into the inside of the motor unit 100 in a state in which the drive shaft is fitted or positioned in a lumen of the reinforcing tube 101. The inner surface of the reinforcing tube 101 (holding member) and the outer surface of the drive shaft 8 are slidable or axially movable relative to one another. As depicted in FIGS. 2, 3, 4A and 4B, the reinforcing tube 101 distally extends to a location in the proximity of the proximal end of the removing member 5.

Here, as depicted in FIGS. 4A and 4B, the proximal end of the drive shaft 8 is connected to a bearing 102, and the bearing 102 is connected to a motor driving unit. A projection member or projection 104 is formed at the proximal end portion or proximal side of the drive shaft 8, and a guide member or guide 103 having a groove along which the projection member 104 is guided is fixed in an internal space 105 of the motor unit 100. The guide member 103 may be fixed to the housing of the motor unit 100. By virtue of the interaction between the guide 103 and the projection 104, the proximal end of the reinforcing tube 101 or holding member is fixed to the housing of the motor unit. The bearing freely 102 rotates only the drive shaft 8 to transmit driving force from the driving source to the drive shaft.

The groove of the guide member 103 is a spiral-shaped groove, and since the drive shaft 8 is acted upon by a pushing-in force (a force pushing toward the distal end or in the distal direction) applied at the proximal end of the drive shaft by the motor driving unit, the projection member 104 is guided spirally by the groove of the guide member 103, whereby the drive shaft 8 itself is rotated. The motor driving unit drives the drive shaft 8 so as to move back and forth. In particular, the drive shaft 8 is acted upon by the driving force from the motor driving unit to perform forward movement while at the same time the drive shaft 8 performs rotational movement as the projection member 104 is guided by the groove of the guide member 103. The movements are transmitted efficiently to the removing member 5 at the distal side, and consequently, also the removing member 5 moves similarly. Consequently, part of the struts 5a of the removing member 5 exhibits a spiral locus. In other words, the removing member 5 rotates in one direction while moving forwardly and rotates in the opposite direction while moving backwardly. By performing the movements successively, the occluding substance can be removed effectively irrespective of the position, size and hardness of the substance.

Since rotational movement of the drive shaft 8 is absorbed by the bearing 102, the rotational force is not transmitted to the motor driving unit side. Preferably, the motor driving unit drives the drive shaft 8 to move back and forth over a distance of 1.0 mm to 5.0 mm. In response to the back and forth movement of the drive shaft 8, the projection member 104 is rotated over 90 degrees to 180 degrees by the guidance of the spiral-shaped groove of the guide member 103. Further, the back and forth driving by the motor driving unit is performed preferably at a frequency of 4 Hz to 2,500 Hz.

The drive shaft 8 is sized and configured, and disposed in a state in which the outer surface of the drive shaft 8 has a small clearance from or is in contact with the inner surface of the reinforcing tube 101. In the present embodiment, since the drive shaft 8 is configured from a super elastic alloy having a high kink resistance such as Ni—Ti and the reinforcing tube 101 is configured from a material having a comparatively high rigidity (i.e., the reinforcing tube 101 has a higher rigidity, and is more rigid, than the drive shaft 8), vibration or wobbling caused by the driving force applied to the drive shaft 8 from the motor driving unit can be absorbed. Especially, where the removing device 4 is disposed on a traveling path having many curves such as a blood vessel, although the influence of vibration or wobbling generated by the driving force applied from the motor driving unit is significant, the influence can be suppressed by the reinforcing tube 101 and the driving force can be transmitted efficiently to the distal side or distal end. The reinforcing tube 101 or a part thereof thus functions as a holding member that suppresses unnecessary movement of the drive shaft 8.

Further, although the size of the reinforcing tube 101 is not restricted particularly, preferably, for example, the outer diameter is set to approximately 1.5 mm to 3.5 mm, the inner diameter to approximately 1.3 mm to 3.3 mm, and the length in the axial direction to approximately 30 cm to 150 cm. The outer diameter of the drive shaft 8 can be set such that the drive shaft 8 contacts the inner surface of the reinforcing tube 101 during sliding movement.

The reinforcing tube 101 has a cylindrical shape of a fixed outer diameter from a proximal end portion to a distal end portion thereof. The reinforcing tube 101 has a three-layer structure configured from an inner layer, an intermediate layer provided on the outer circumference of the inner layer, and an outer layer provided on the outer circumference of the intermediate layer. The reinforcing tube 101 has flexibility such that, when it is inserted into a blood vessel, it can be bent freely along the curves of the blood vessel.

Preferably, the inner layer of the reinforcing tube 101 is configured from a low friction material. Examples of the constituent material of the inner layer include fluorine-based resins such as, polytetrafluoro-ethylene and so forth.

Further, the intermediate layer of the reinforcing tube 101 is preferably configured so as to function as a reinforcing member. Examples of the constituent material of the intermediate layer include stainless steel, tungsten, nickel, titanium, a nickel-titanium alloy, a nickel-cobalt alloy, a nickel-manganese alloy, carbon fiber and so forth. In other words, the intermediate layer is preferably configured from, for example, a mesh in which predetermined wires such as metal wires, carbon fiber and so forth described hereinabove are interwoven.

Examples of the constituent material of the outer layer of the reinforcing tube 101, for example, polyester such as polyether ether ketone, polyethylene terephthalate or polybutylene terephthalate, polyimide, polyamide, polyether polyamide, polyester polyamide, acrylonitrile-butadiene-styrene (ABS) resins, acrylonitrile-styrene (AS) resins, and fluorine-based resins such as polytetrafluoro-ethylene. Further, blends of two or more of the materials mentioned or layers of two or more of the materials may be used.

Such a reinforcing tube 101 as described above preferably has an enhanced X-ray contrast property at least at a distal end portion of the tube 101 such that it can be visually recognized, upon removal of an occluding substance in a blood vessel, under X-ray fluoroscopy. In this case, for example, an X-ray opaque material such as barium sulfate, platinum, gold or tungsten may be blended in the constituent material at least of the outer layer or an X-ray contrast region constituted from the X-ray opaque material described hereinabove may be provided.

Figure 5A:
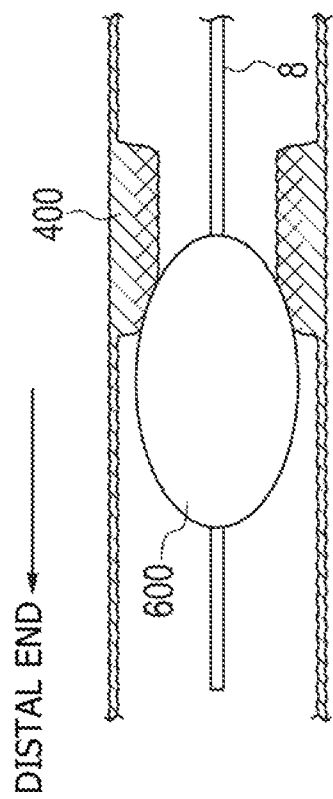
FIGS. 5A, 5B, 5C and 5D are diagrammatic views illustrating a manner in which the removing member depicted in FIG. 1 is used in a living body lumen.
Figure 5C:
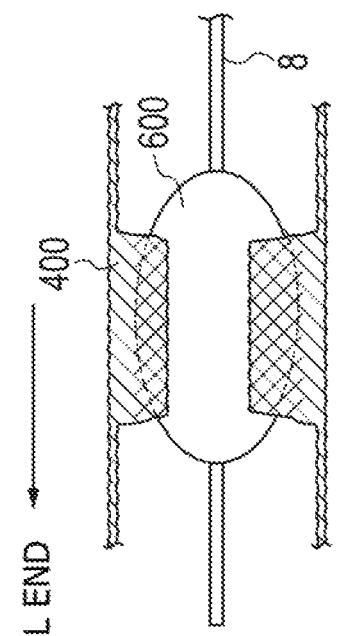
Figure 5B:
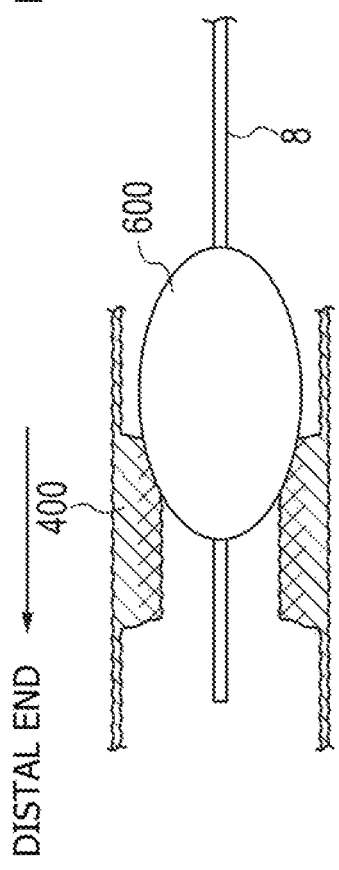
Figure 5D:
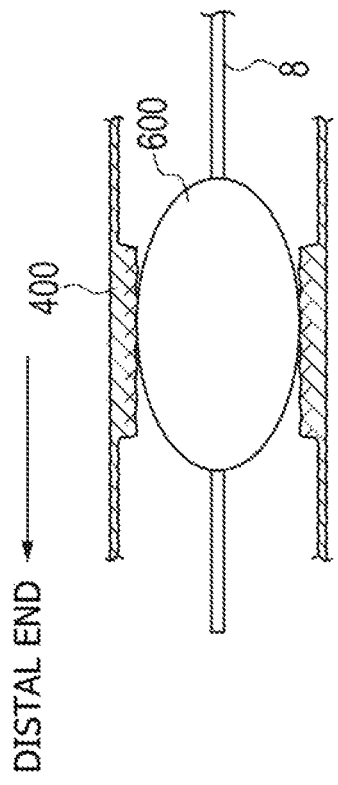

Next, the operation or action of the catheter system 1 is described with reference to the diagrammatic views of a lesion depicted in FIGS. 5A to 5D. If the removing device 4 comes to a lesion affected area, then the distal side or distal end of the removing member 5 is brought into contact with a stenosis 400 as depicted in FIG. 5A. Here, driving or operating the motor driving unit causes the removing member 5 to perform a rotational movement while also axially moving back and forth, and therefore, the stenosis 400 is removed by the struts 5a of the removing member 5. Here, since the removing member 5 is shaped or configured such that the removing member 5 is self-expanded in a radial direction, a pressing force equal to or higher than a predetermined level can be normally applied to the stenosis 400, and therefore, treatment which does not rely upon the position, size and hardness of the stenosis can be anticipated. Further, inserting the removing member 5 into the inside of the stenosis 400 as depicted in FIG. 5B allows the outermost diameter portion (greatest outer diameter portion) of the removing member 5 to contact the stenosis 400, and consequently, by driving of the motor driving unit, the stenosis 400 can be removed. Further, positioning the removing member 5 at the peripheral side or distal side in the blood vessel with respect to the stenosis 400 and then operating the removing member 5 so that the removing member 5 is pulled back to the proximal side or proximal direction as depicted in FIG. 5C, the proximal side or proximal end portion of the removing member 5 contacts the stenosis 400. Then, operating or driving the motor driving unit in this state, the stenosis 400 can be removed similarly. Also it is possible to dispose the removing member 5 in a state in which the stenosis 400 is sandwiched between the struts 5a of the removing member 5 as depicted in FIG. 5D. In this state, driving or operating the motor driving unit will result in the stenosis 400 being cut or removed.

Consequently, since the occluding substance at the stenosis 400 can be removed, it is possible to place the blood vessel into a communication state to assure blood flow and form a path for various devices to be used at succeeding treatment steps. Consequently, the succeeding treatment steps (expansion treatment by a balloon catheter, expansion by a stent or the like, and so forth) can be performed readily.

Further, since the plurality of diamond-shaped holes 5c are formed at thin board portions of the struts 5a of the removing member 5 according to the present embodiment, an occluding substance of the stenosis 400 can be scraped off by the aforementioned rotational operation. Therefore, the stenosis 400 can be opened effectively.

Further, since one of the distal end part 6 and the proximal end part 7 of the removing member 5 is fixed to the drive shaft 8, at the side of the removing member 5 at which the part is fixed, rotational force and expanding force can be transmitted with certainty to the stenosis 400. On the other hand, at the side of the removing member 5 at which the part is not fixed, when the removing member 5 is inserted into a narrow stenosis, one of the distal end part 6 and the proximal end part 7 which is not fixed slidably moves on the drive shaft 8, and therefore, insertion of the removing member 5 into the stenosis 400 is facilitated.

FIG. 6 depicts an example of a filter device 300 which can be used together with the removing member 5 when treatment of the stenosis 400 by the removing member 5 is performed.

The filter device 300 includes a filter tool 310 having a function as a filter, and a sheath 320 which can accommodate the filter tool 310 therein.

The filter tool 310 includes a filter portion (filter) 311 braided from a plurality of strands, and an elongate shaft portion 313 extending through the filter portion 311 and interlocked with the filter portion 311.

The filter portion 311 can be contracted when it is accommodated in the sheath 320 and can be expanded by its self-expanding force when it is taken out from the sheath 320. The filter portion 311 is configured such that the distal side of the filter portion 311 has a closed-cage-like shape and is interlocked with the shaft portion 313 and, at the proximal side of the filter portion 311, the plurality of strands are twisted together and interlocked with the shaft portion 313.

The outer diameter of each strand forming the filter portion 311 can be suitably selected depending upon the material, application and so forth of the strands. As an example, the outer diameter of each strand may be 20 μm to 100 μm, and can preferably be 40 μm.

Preferably, the constituent material forming the strands is a material having flexibility, and, for example, shape-memory alloys to which a shape-memory effect or super elasticity is applied by heat treatment, stainless steel, Ta, Ti, Pt, Au, W, polyolefin such as polyethylene or polypropylene, polyamide, polyester such as polyethylene terephthalate, fluorine-based polymers such as ethylene tetrafluoroethylene (ETFE), polyether ether ketone (PEEK), polyimide and so forth can be used suitably. As a shape-memory alloy, Ni—Ti-based, Cu—Al—Ni-based and Cu—Zn—Al-based alloys or combinations of them are used preferably. As a structure of a combination of a plurality of materials, for example, a structure that Ni—Ti alloy is coated on a core wire made of PT in order to provide a contrast property and another structure that a core wire made of Ni—Ti alloy is plated with gold are listed.

Although the constituent material of the shaft portion 313 is not particularly limited, examples of suitable materials include stainless steel, shape-memory alloys and so forth.

The sheath 320 includes a tube 321, a hub 322 and a kink-resisting protector 323. The tube 321 includes a lumen 324 into which the filter tool 310 can be accommodated, and is open at a tube opening 326 formed at a distal side end portion of the tube. The hub 322 is fixed to a proximal side end portion of the tube 321 and has a hub opening 325 communicating with the lumen 324. The kink-resisting protector 323 is a flexible member which covers the interlock portion between the tube 321 and the hub 322 and suppresses a kink of the tube 321.

The constituent material forming the tube 321 is not particularly limited, but examples of materials include polyolefin such as polyethylene, polypropylene, ethylene-propylene copolymer or ethylene-vinyl acetate copolymer, polyvinyl chloride, polystyrene, polyamide, polyimide or combinations of them.

FIG. 7 illustrates an example of use of the filter device 300.

Prior to use of the filter device 300, an introducer sheath (not depicted) is inserted percutaneously into a blood vessel, and a guide wire (not depicted) is inserted into the blood vessel through the introducer sheath. Then, the guide wire is pushed forwardly until it comes to the near position side with respect to the stenosis 400 (i.e., the guide wire is pushed forward to a position on the proximal side of the stenosis 400) Thereafter, a guiding catheter 340 is inserted along the guide wire into the blood vessel until it comes to the near position side (proximal side) with respect to the stenosis 400. Then, a support catheter (not depicted) is fitted into the guiding catheter 340 until the support catheter and the guide wire come to the remote position side (far side or distal side) with respect to the stenosis 400. Thereafter, the filter device 300 is inserted into the blood vessel through the support catheter until the filter portion 311 is positioned at the remote position side (far side or distal side) with respect to the stenosis 400. The guide wire and the support catheter are pulled out suitably.

The filter device 300 is prepared, prior to introducing the filter device into a living body, in a state in which the filter tool 310 is accommodated in the sheath 320. Then, after the filter portion 311 is moved to the remote position side with respect to the stenosis 400, the sheath 320 is relatively moved to the near position side with respect to the filter tool 310 so that the filter portion 311 is positioned on the remote position side from the tube 321 (i.e., so that the filter tool 310 projects distally beyond the distal end of the tube 321. Consequently, as depicted in FIG. 7, the filter portion 311 is placed into an expanded state by the self-restoring force of the filter device 310 and the outer circumference or outer surface of the filter portion 311 having shifted to a cage-like shape contacts the inner wall surface of the blood vessel. At this time, the filter portion 311 is placed into a state in which it is open toward the stenosis 400 located at the upstream side of the blood flow (at the near position side). Thereafter, the sheath 320 is pulled out while the filter tool 310 is left in the blood vessel.

The removing member 5 is prepared in a state in which it is accommodated in the outer catheter 2 and is moved into a blood vessel through the guiding catheter 340. When the removing member 5 is to be introduced into the blood vessel, the shaft portion 313 of the filter tool 310 is fitted into the guide wire lumen of the drive shaft 8 and the removing member 5 is delivered along the shaft portion 313.

Carrying out the above-described various treatments (refer to FIGS. 5A to 5D) by the removing member 5 in the state in which the filter portion 311 is disposed at the remote position side (distal end or distal side) of the removing member 5 as depicted in FIG. 7, an occluding substance of the stenosis 400 can be scraped off. Then, substances (debris) generated by the scraping off of the occluding substance are collected and removed by the filter portion 311. Accordingly, it is possible to suppress the possibility that debris will flow to the peripheral side of the blood vessel to cause a new stenosis or occluding portion.

Next, a different form of the aforementioned removing member 5 is described. Like elements to those described above are denoted by like reference symbols and a detailed description of such features is not repeated to avoid redundancy.

FIG. 8 is a lateral view depicting a removing member 50 (expandable member) according to the different form, and FIG. 9 is a view depicting an appearance perspective view of the removing member 50 according to the different form in an enlarged scale.

As depicted in FIGS. 8 and 9, the removing member 50 according to the different form is different from the aforementioned removing member 5 in that projections 50d are formed on each strut 50a.

Since the projections 50d are formed partly at a thin board portion 50e of the strut 50a as in the case of the removing member 50 according to the present form, an occluding substance in the stenosis 400 can be scraped off by driving movement by the above-described motor driving unit, and therefore, the stenosis 400 can be opened effectively.

Modifications to the aforementioned removing member 5 are now described. Like elements to those described above are denoted by like reference symbols and a detailed description of such features is not repeated to avoid redundancy.

As depicted in FIG. 10, a removing member 60 (expandable member) according to a modification to the removing member 5 depicted in FIGS. 2 and 3 does not have the holes 5c and the circumferentially projecting protrusions formed at a proximal side half portion of each strut 60a. In this regard, the removing member 60 is different from the removing member 5.

By configuring the removing member 60 in such a manner as described above, when the removing member 60 is moved back, the removing member 60 can be prevented from being caught by a lesion affected area or the outer catheter 2, and damage to the catheter system 1 can be prevented.

As depicted in FIG. 11, a removing member 70 (expandable member) according to a modification to the removing member 50 depicted in FIGS. 8 and 9 does not have the projections 50d formed at a proximal side half portion of each strut 70a. In this regard, the removing member 70 is different from the removing member 50.

By configuring the removing member 70 in this manner, the removing member 70 can exhibit similar effects to those of the removing member 60 according to the preceding modification.

A modification to the removing member 60 depicted in FIG. 10 is described with reference to FIG. 12. Like elements to those described hereinabove are denoted by like reference symbols and overlapping description of them is omitted herein to avoid redundancy.

As depicted In FIG. 12, a removing member 80 (expandable member) according to the present modification has a filter member 81 provided at a distal side half portion of the removing member 80 in such a manner as to cover a portion of the removing member 80 to the most distal end. In this regard, the removing member 80 is different from the removing member 60.

Where the removing member 80 is configured in such a manner as described above, an occluding substance is treated using a proximal side half portion (proximal side portion) of the removing member 80. By driving the motor driving unit in a state in which the proximal side portion of the removing member 80 contacts the occluding substance, removal of the occluding substance is performed by the proximal side portion of the removing member 80, and the removed occluding substance (debris) is collected by the filter member 81 which covers the distal side of the removing member 80. Consequently, the removed occluding substance may be prevented from flowing to the peripheral side (distal direction) by the blood flow in the blood vessel.

Further, by configuring the removing member 80 such that the distal end part 6 at the side of the removing member 80 at which the filter member 81 is disposed is not fixed to the drive shaft 8 while the proximal end part 7 at the side of a proximal end portion of the removing member 80 is fixed to the drive shaft 8, when the distal side of the removing member 80 is to be inserted into the stenosis 400, the distal end part 6 is slidably moved to facilitate the insertion, and when the stenosis 400 is to be treated by the proximal side of the removing member 80, since the proximal end part 7 does not slidably move, the expanding force can be transmitted with certainty to the stenosis 400.

FIG. 13 illustrates another modification of the removing member 90 (expandable member) that is similar to the removing member 50 shown in FIGS. 8 and 9, but provided with a filter member 91 at the distal side half portion of the removing member 90. The filter member 91 is similar to the filter member 81 described above and shown in FIG. 12.

Second Embodiment

Another embodiment of the catheter system is now described with reference to FIGS. 14-17. Lie elements to those described above in connection with the aforementioned embodiment are denoted by like reference symbols and a detailed description of such features is not repeated to avoid redundancy.

Figure 14:
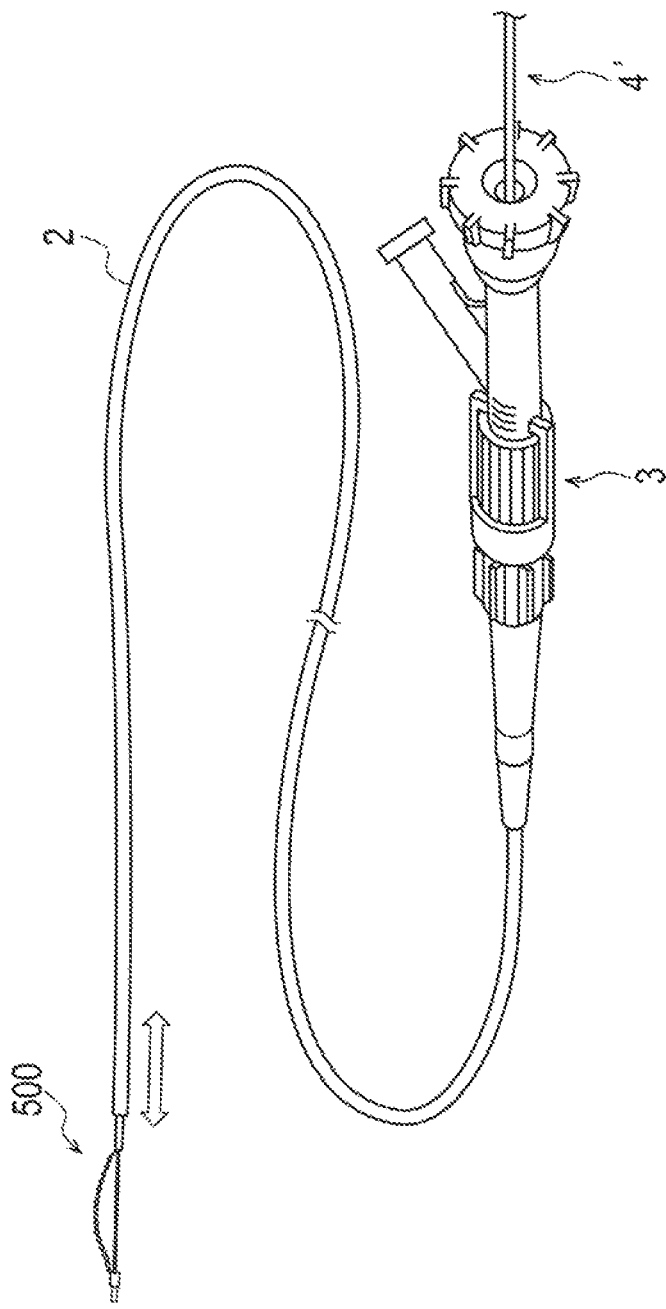
FIG. 14 is a schematic view depicting another embodiment of the catheter system.
Figure 15:
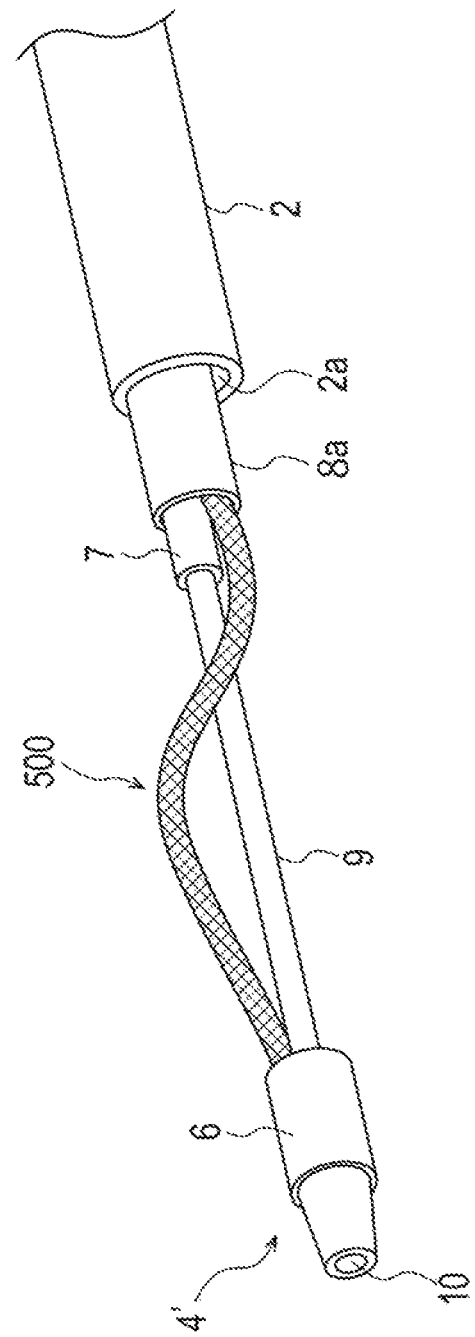
FIG. 15 is a perspective view of a form of a removing member depicted in FIG. 14.
Figure 16:
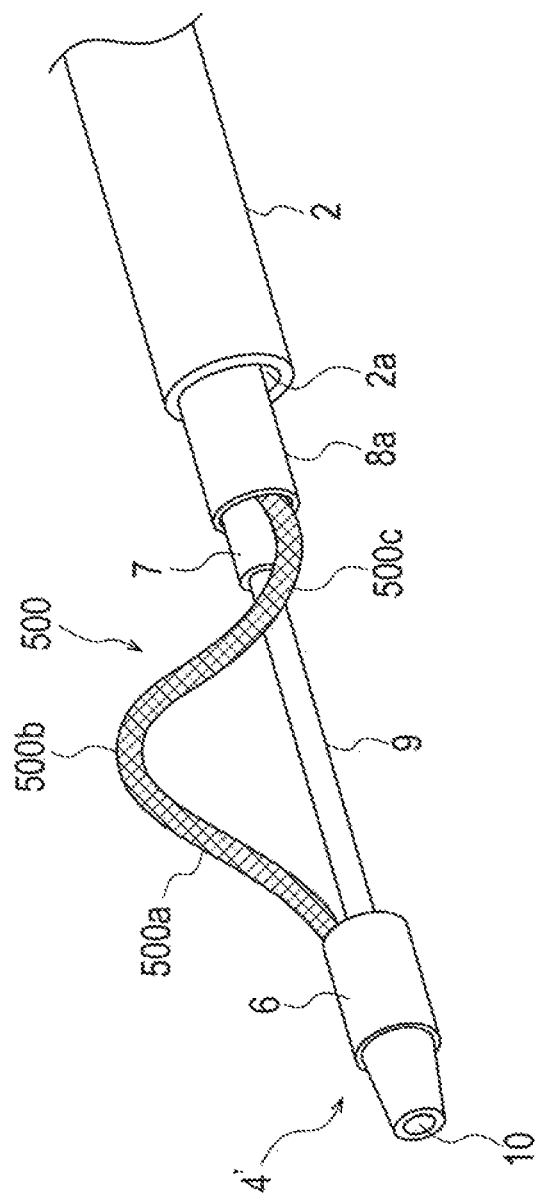
FIG. 16 is a perspective view depicting the removing member depicted in FIG. 15 in a state in which the removing member is swollen.
Figure 17:
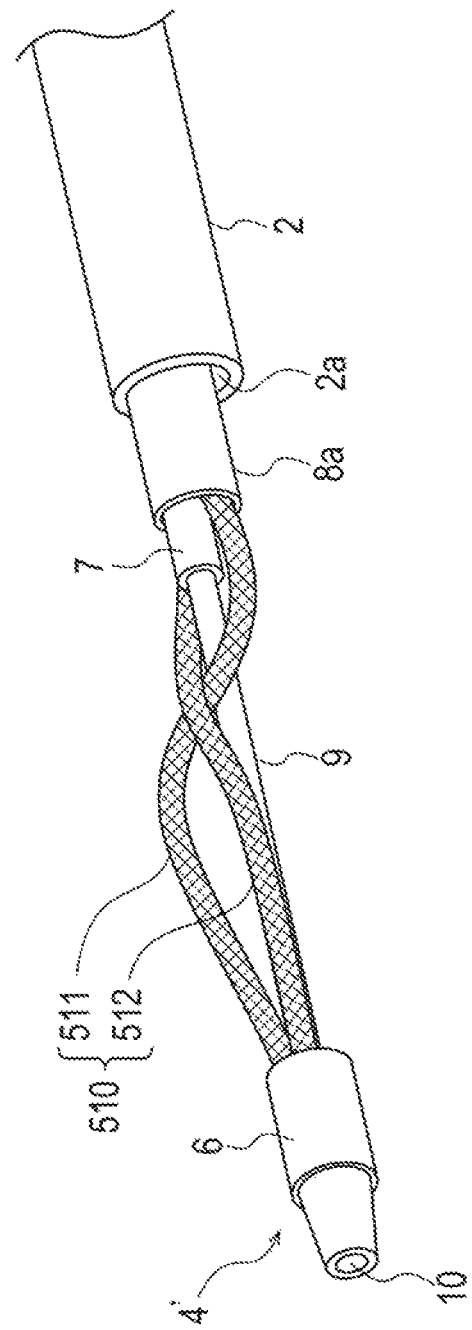
FIG. 17 is a schematic view depicting a modification to the removing member depicted in FIG. 15.
Figure 18:
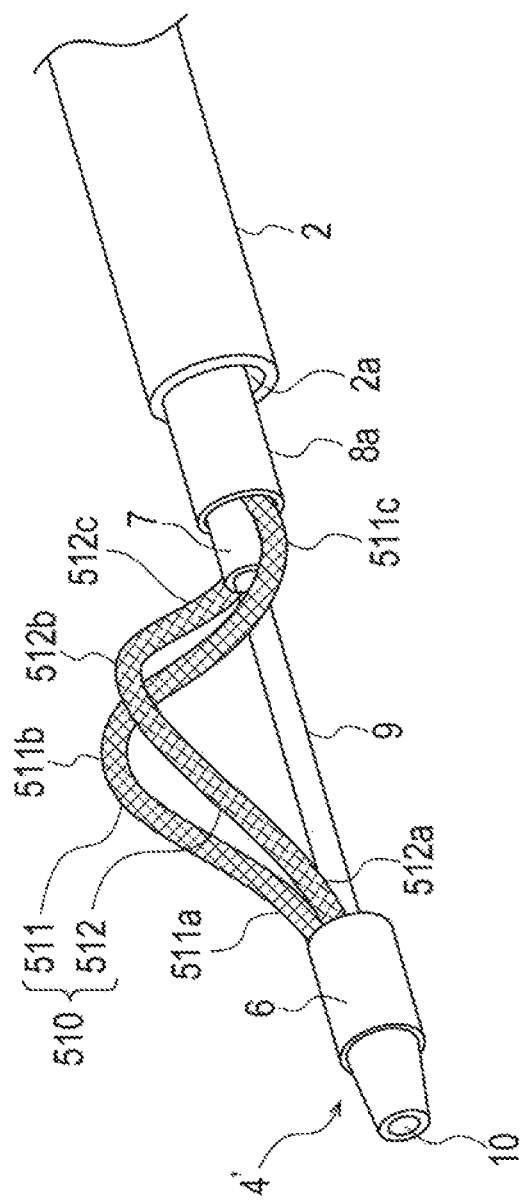
FIG. 18 is a perspective view depicting the removing member depicted in FIG. 17 in a state in which the removing member is swollen.

FIG. 14 is a lateral view depicting a catheter system 1' according to the present embodiment, FIG. 15 is a perspective view of a removing member 500 (expandable member) of a removing device 4' depicted in FIG. 14, and FIG. 16 is a perspective view depicting the removing member 500 depicted in FIG. 15 in a state in which the removing member 500 is swollen. FIG. 17 is a perspective view of a removing member 510 according to a modification to the removing member 500 depicted in FIG. 15, and FIG. 18 is a perspective view depicting the removing member 510 depicted in FIG. 17 in a state in which the removing member 510 is swollen.

As depicted in FIG. 14, the catheter system 1' includes an outer catheter 2, a hub 3 provided at a proximal end portion of the outer catheter 2, the removing device 4' fitted in the outer catheter 2 for rotation around an axis and for movement in an axial direction with respect to the outer catheter 2, and the removing member 500 (which corresponds to a "grinding member") disposed at the distal side or distal end of the removing device 4' and configured to drill and remove an occluding substance which constricts or occludes a vascular lumen. The occluding substance includes not only a substance which occludes a vascular lumen but also various substances which constrict the lumen even if they do not fully occlude the lumen. In particular, examples of the occluding substances include thrombi, fatty streaks, plaques, calcified lesions, intimal hypertrophy, arteriosclerosis layers and so forth.

As depicted in FIG. 15, the removing member 500 for removing an occluding substance generated in a blood vessel is fixed to a distal end portion of the removing device 4'.

The removing member 500 is configured such that it can be deformed, when the outer catheter 2 is operated so as to move in directions indicated by a double-side arrow mark in FIG. 14, between a state in which the removing member 500 is accommodated in the outer catheter 2 and has a reduced outer diameter and a swollen state in which it projects distally from a distal end opening 2a of the outer catheter 2 and is swollen or expanded in a radial direction as depicted in FIGS. 15 and 16. When an occluding substance is to be removed by the removing member 500, the removing member 500 is operated so as to project distally from the distal end opening 2a of the outer catheter 2 and is shifted into the swollen state by a proximal side operation hereinafter described, and then treatment for removing the occluding substance is performed by the removing member 500.

In the following, the removing member 500 when it is in the swollen state is described.

As depicted in FIGS. 15 and 16, the removing member 500 can be configured from, for example, a single strand having relatively high rigidity and fixed to a distal end part 6, a proximal end part (proximal end tube) 7, and an outer tube 8a.

A guide wire shaft 9 is fitted in a slidably movable state in the proximal end part 7. The outer surface of the proximal end part 7, the proximal end of the removing member 500 and the inner surface of the outer tube 8a are fixed to each other by adhesion. The guide wire shaft 9 extends to the proximal end in the outer tube 8a such that the guide wire shaft 9 can be operated by a user from the hand side (proximal side) of the guide wire shaft 9. Further, the distal side of the guide wire lumen 9 passes through the inside of the distal end part 6 and is open at a distal end opening 10. By such a configuration as described above, operating the outer tube 8a to advance to the distal side or in the distal direction in a state in which the guide wire shaft 9 is fixed at the hand side (proximal end) results in the proximal end part 7 slidably moves on the guide wire shaft 9, which can reduce the distance between the distal end part 6 and the proximal end part 7. Further, the removing member 500 is fixed in a positional relationship twisted by 180 degrees from a linear state between the distal side and the proximal side of the removing member 500. That is, between the distal end part 6 and the proximal end part 7, the removing member is twisted 180 degrees.

The outer tube 8a is connected at the proximal end thereof, for example, to a motor driving unit of the aforementioned motor unit 100 (refer to FIGS. 4A and 4B). As the motor driving unit, for example, a known driving member which can perform piston movements is used. When the motor driving unit is driven, the outer tube 8a slidably moves (oscillates) in the forward and rearward directions (axially) in the lumen of the outer catheter 2, and also the removing member 500 disposed at the distal side or distal end of the outer tube 8a slidably moves (oscillates) similarly.

As depicted in FIG. 16, the removing member 500 has three regions including a distal end region 500a, an intermediate region 500b and a proximal end region 500c disposed in that order from the distal side (distal end) to the proximal side (proximal end). Operating the proximal end (hand side) of the removing member 500 to reduce the distance between the distal end part 6 and the proximal end part 7 results in the intermediate region 500b of the removing member 500 being acted upon by forces pushing in from both of the distal end region 500a side and the proximal end region 500c side (axial forces directed towards one another), whereupon the intermediate region 500b is swollen or expanded to the outer side in a radial direction.

The constituent material forming the removing member 500 is preferably a metal material having a high rigidity such as cobalt chrome is used. In the present embodiment, the removing member 500 is configured such that six small-diameter strands of cobalt chrome are wound spirally around a metal wire configured from the same material. By such a configuration as described above, a large number of fine recesses and projections are formed, and the recesses and projections make it possible to effectively remove an occluding substance which forms a stenosis or an occlusion.

An example of a method of use of the catheter system 1' is now described. When treatment for removing an occluding substance in a blood vessel is to be performed, the removing device 4' having the removing member 500 disposed at the distal side or distal end of the removing device 4' is fitted in advance in the outer catheter 2, and the removing member 500 is accommodated in a substantially linear state inside the distal side (distal end) of the outer catheter 2. Then, a guide wire inserted in the guide wire shaft 9 (in the lumen of the guide wire shaft 9) is moved in the forward direction, and the removing device 4' and the outer catheter 2 are moved tracing the guide wire so that the removing device 4' and the outer catheter 2 are inserted to or positioned at a target region in the blood vessel. The situation at this time is monitored by X-ray contrast or the like.

Then, in a state in which the outer catheter 2 is fixed at its proximal side so as not to move, the removing device 4' disposed in the outer catheter 2 is pushed to move to the peripheral side (in the forward or distal direction) in the blood vessel. Consequently, the removing member 500 is placed into a state in which it projects from the distal end opening 2a of the outer catheter 2 as depicted in FIGS. 15 and 16.

Then, in a state in which the guide wire shaft 9 is fixed, the outer tube 8a (which corresponds to a "slide member") is pushed to move to the distal side or in the forward/distal direction. Consequently, the distance between the distal end part 6 and the proximal end part 7 decreases and the intermediate region 500b of the removing member 500 is swollen or expands. In this state, the intermediate region 500b is contacted with the stenosis 400 in the blood vessel and the aforementioned motor driving unit is driven. Consequently, the removing member 500 slidably moves (oscillates) in the forward and rearward directions (axially back and forth) to remove the occluding substance which forms a stenosis or an occlusion (refer to, for example, FIGS. 5A to 5D). Further, if the operator rotationally operates the removing device 4' which is in axial back and forth movement, then the occluding substance can be removed over the circumferential direction in the blood vessel. Where the removing member 500 is fixed in a state rotated by 180 degrees in a counterclockwise direction as depicted in FIGS. 15 and 16 (i.e., wrapped 180 degrees around the guide shaft 9 in a counterclockwise direction), the operator can efficiently transmit force to the stenosis 400 by performing a rotational operation in the counterclockwise direction.

When treatment for the stenosis 400 is performed, also it is possible to use the aforementioned filter device 300 together with the catheter system 1' (refer to FIG. 7). Substances (debris) generated by scraping off of the occluding substance can be collected by the filter portion 311.

As described above, with the catheter system 1', the removing member 500 can be inserted to a position close to a stenosis of a blood vessel and the intermediate region 500b is swollen or expanded so as to contact the occluding substance which constricts the inside of the blood vessel and then, in this state, the motor driving unit can be driven to perform a sliding (oscillation) movement (axial movement) while a rotating operation in a circumferential direction of the blood vessel is performed for the removing member 500 As a result, the occluding substance in the stenosis can be gradually drilled and removed by the intermediate region 500b. Therefore, the occluding substance can be drilled and removed readily, rapidly and with certainty.

Consequently, since the occluding substance in the stenosis 400 can be removed, the blood vessel can be placed into communication to assure blood flow and a path for various devices to be used at succeeding treatment steps can be formed. Consequently, the succeeding treatment steps (expansion treatment by a balloon catheter, expansion by a stent or the like, and so forth) can be performed readily.

Further, since the removing member 500 according to the present embodiment is formed from a multiple stranded wire, a great number of fine recesses and projections are formed on the outer surface of the removing member 500, and therefore, an occluding substance in the stenosis 400 can be efficiently scraped off by an aforementioned sliding (oscillating) operation. Further, since the removing member 500 is fixed in such a twisted positional relationship that the distal side and the proximal side of the removing member 500 sandwich the guide wire shaft 9 therebetween, by rotating the removing member 500, the removing member 500 is supported by the guide wire lumen 9 and rotation from the hand side can be transmitted with certainty. Consequently, the removing member 500 can be caused to act so as to be screwed into the occluding substance along the direction of rotation, and consequently, the occluding substance can be scraped off more effectively. This embodiment can also include a holding member like the holding member described above with respect to the embodiment and modifications shown in FIGS. 1-13 to suppress unnecessary movement of the drive shaft.

A modification to the removing member 500 depicted in FIG. 15 is next described. Like elements to those described above in connection with the aforementioned embodiment are denoted by like reference symbols and a detailed description of such features is not repeated to avoid redundancy.

FIG. 17 is a perspective view depicting a removing member 510 according to the modification, and FIG. 18 is a perspective view of the removing member 510 in a swollen state.

As depicted in FIGS. 17 and 18, the removing member 510 according to the modification differs from the aforementioned removing member 500 in that two removing members including one removing member 511 and another removing member 512 are disposed in a crossing relationship with each other. The proximal end of the removing member 511 and the proximal end of the removing member 512 are fixed by adhesion in a mutually crossing state to the outer surface of the proximal end part 7 and the inner surface of the outer tube 8a. The removing member 511 has a distal end region 511a, an intermediate region 511b and a proximal end region 511c while the removing member 512 has a distal end region 512a, an intermediate region 512b and a proximal end region 512c. In a manner similar to the removing member 500 described above, by pushing the outer tube 8a into the distal side in a state in which the guide wire lumen 9 is fixed at the hand side, the intermediate region 511b and the intermediate region 512b are swollen or expanded radially outwardly.

Where the one removing member 511 and the other removing member 512 are disposed in a mutually crossing relationship as in the case of the removing member 510 according to the present modification, if the above-described rotational operation is performed by the operator, then the removing members 511 and 512 support each other, and therefore, an operation which does not rely upon the direction of rotation can be employed, namely, a reduction in the removing efficiency of the stenosis 400 by an influence of the direction of rotation can be suppressed. Further, since the one removing member 511 and the other removing member 512 cross each other at the respective intermediate regions 511b and 512b, when the intermediate regions 511b and 512b are swollen or expanded, the supporting force acting between the intermediate regions 511b and 512b can be raised. Consequently, it is possible to more effectively suppress a drop of the removing efficiency of the stenosis 400. Further, since the one removing member 511 and the other removing member 512 are fixed at their respective proximal ends to the outer tube 8a in the state in which they cross with each other, the intermediate regions 511b and 512b of the removing members 511 and 512 can be swollen or expanded simultaneously by an operation for moving the outer tube 8a toward the distal end or direction, and the intermediate regions 511b and 512b of the removing members 511 and 512 can be contracted simultaneously by an operation that moves the outer tube 8a toward the proximal end or direction. Therefore, time and effort for performing a work for expanding or contracting the intermediate regions 511b and 512b individually can be omitted, and a smooth technique can be implemented.

Third Embodiment

A further embodiment of the catheter system is now described. Like elements to those described above in connection with the earlier embodiments are denoted by like reference symbols and a detailed description of such features is not repeated to avoid redundancy.

Figure 19:
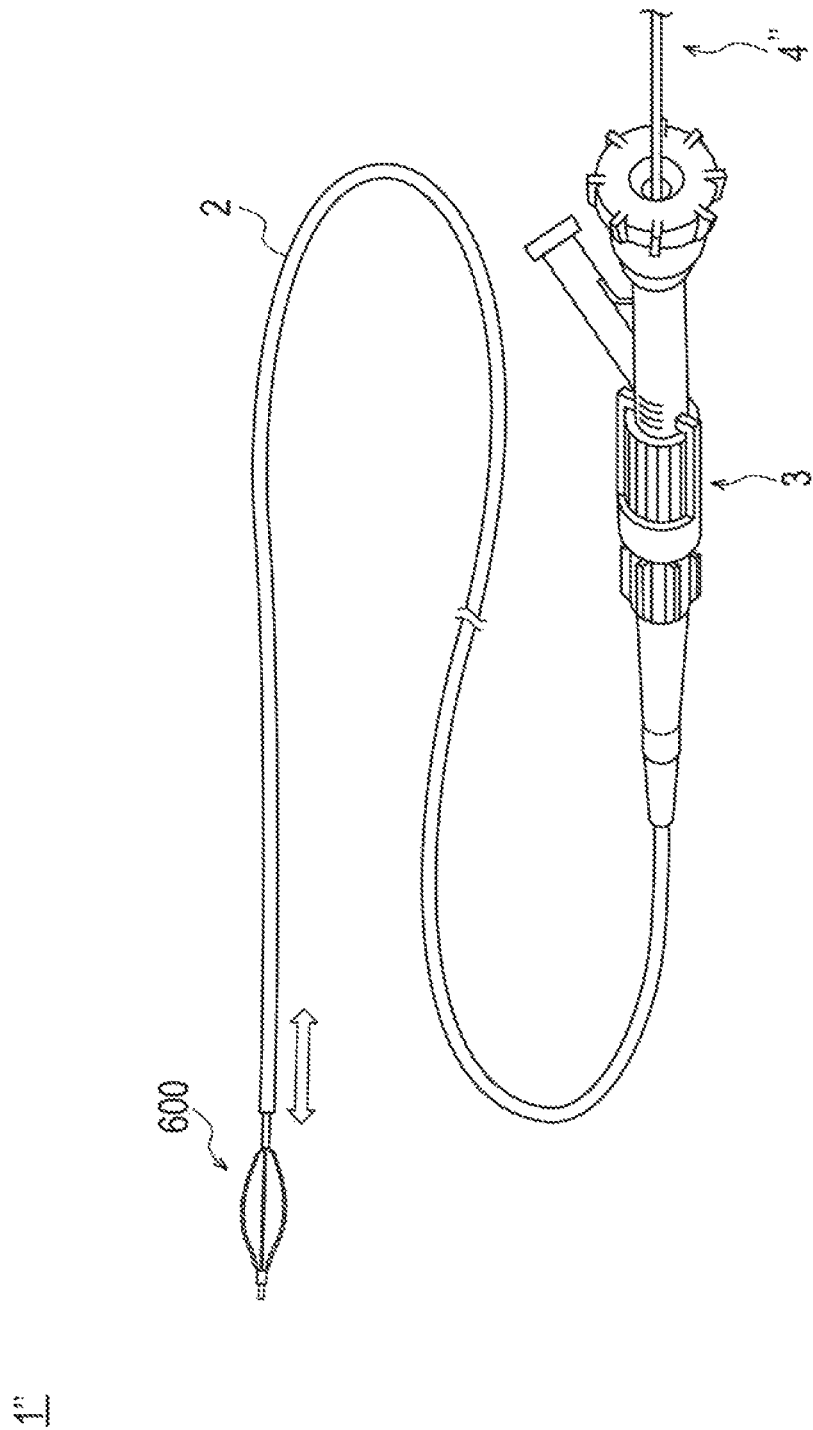
FIG. 19 is a schematic view depicting a further embodiment of the catheter system.
Figure 20:
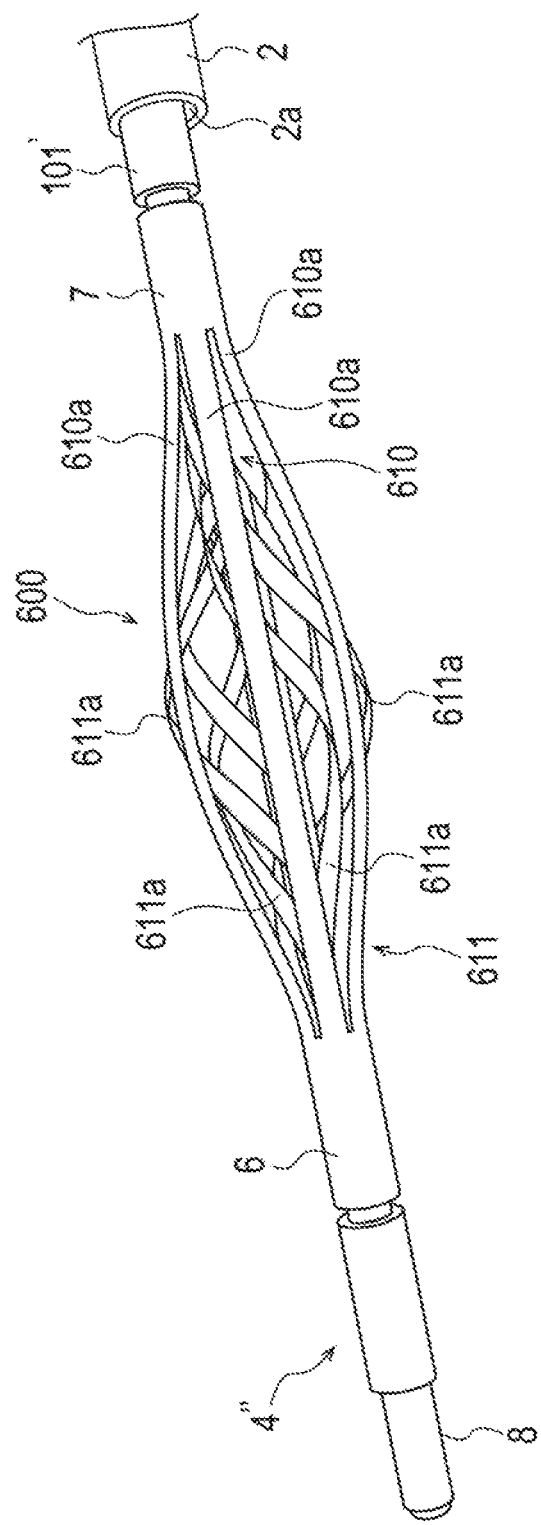
FIG. 20 is a schematic view depicting a form of a removing member depicted in FIG. 19.
Figure 21:
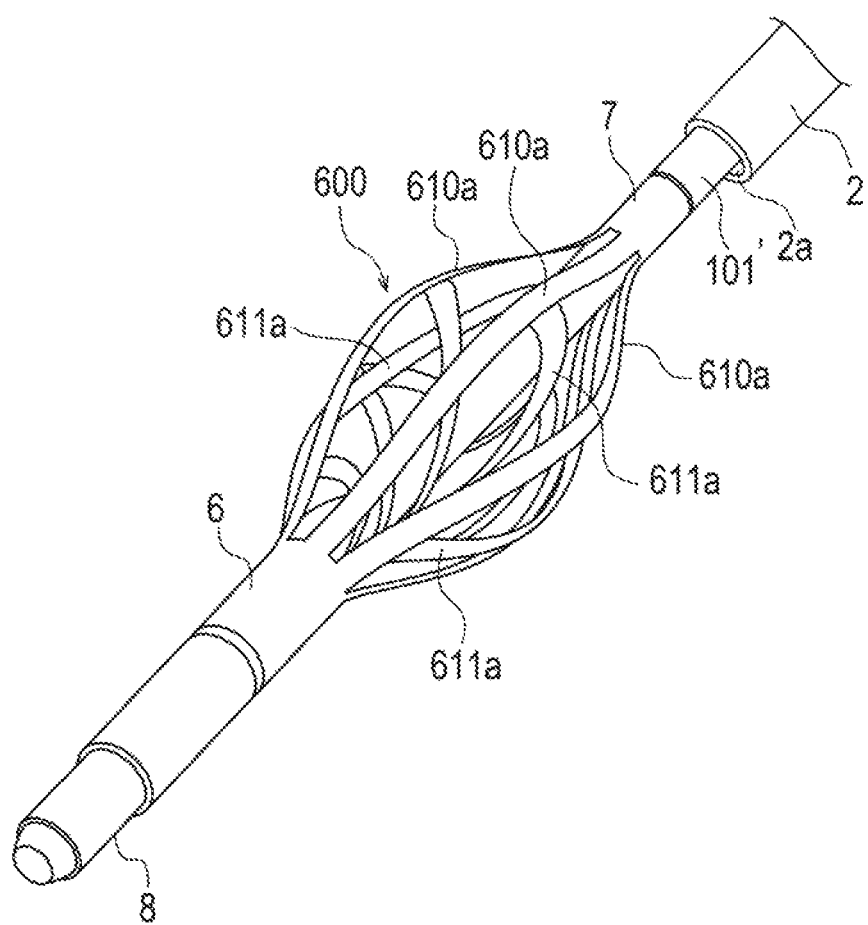
FIG. 21 is a perspective view of the removing member depicted in FIG. 20.
Figure 22A:
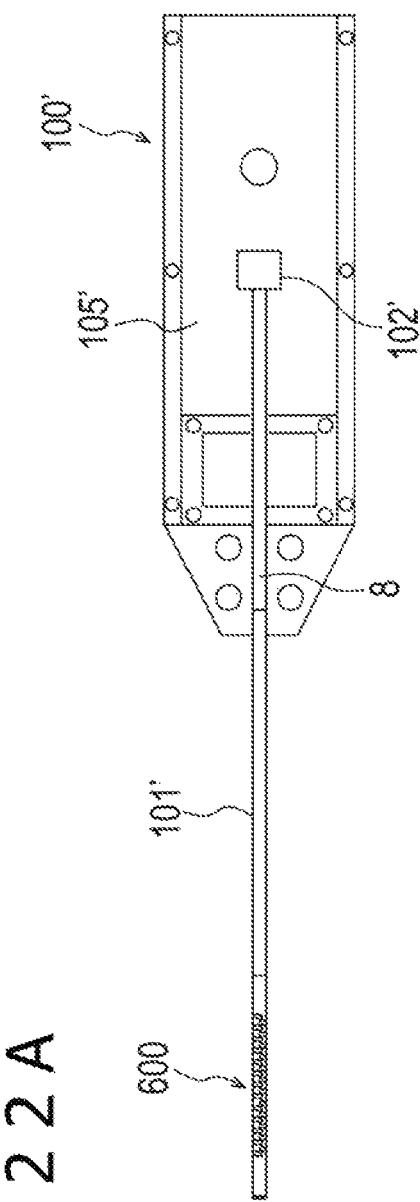
FIG. 22A is a schematic view depicting a motor unit of the catheter system.
Figure 22B:
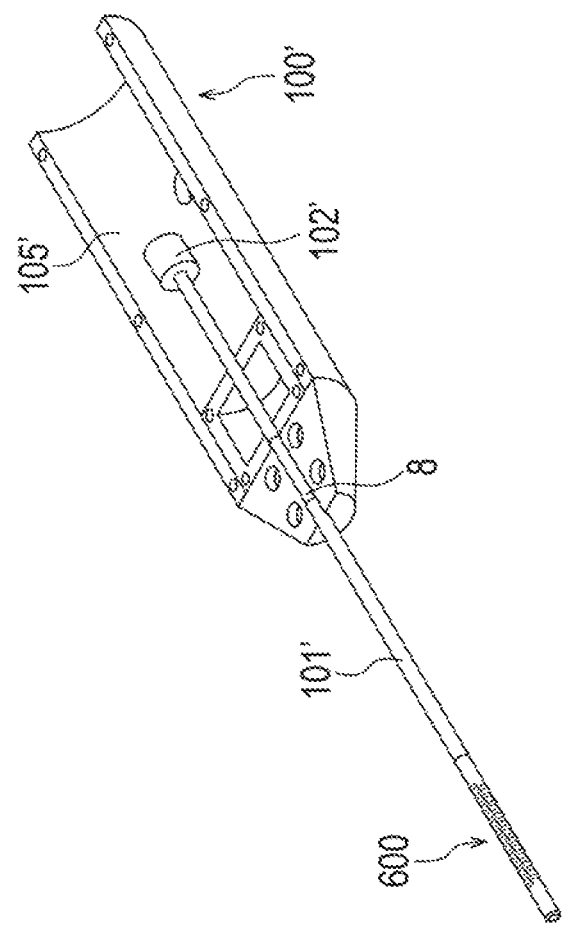
FIG. 22B is a perspective view of the motor unit depicted in FIG. 22A.
Figure 23A:
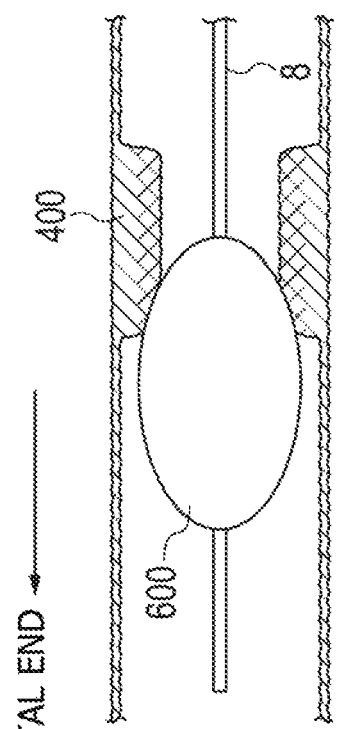
FIGS. 23A, 23B, 23C and 23D are diagrammatic views illustrating a manner in which the removing member depicted in FIG. 19 is used in a living body lumen.
Figure 23B:
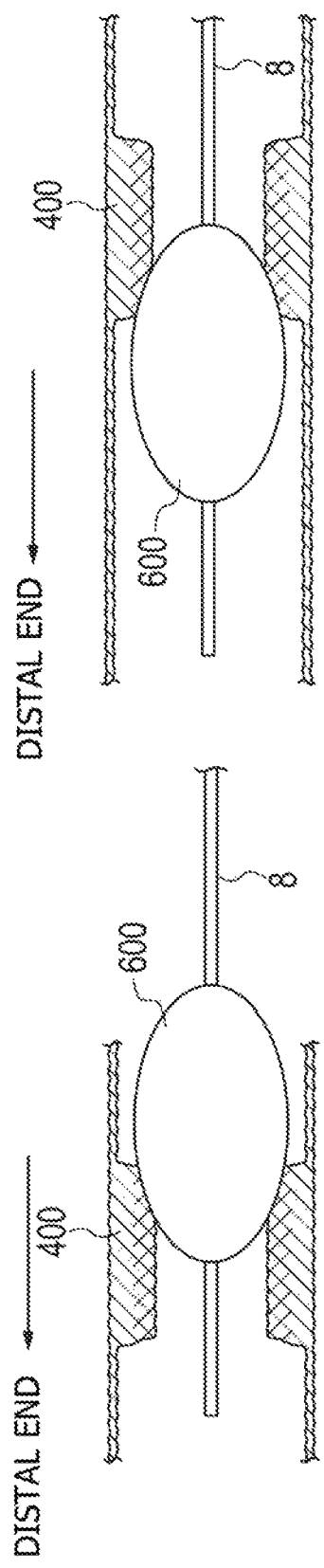
Figure 23C:
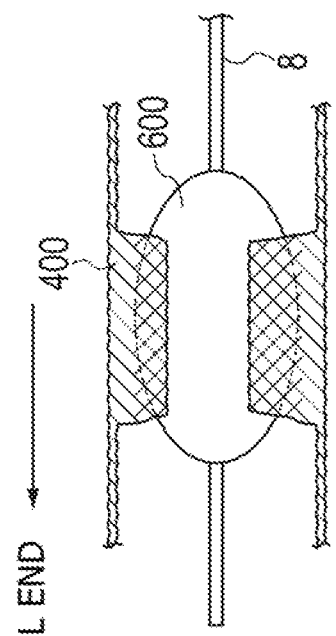
Figure 23D:
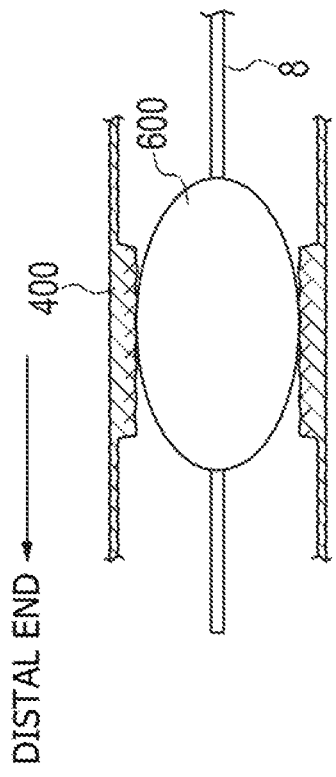
Figure 24:
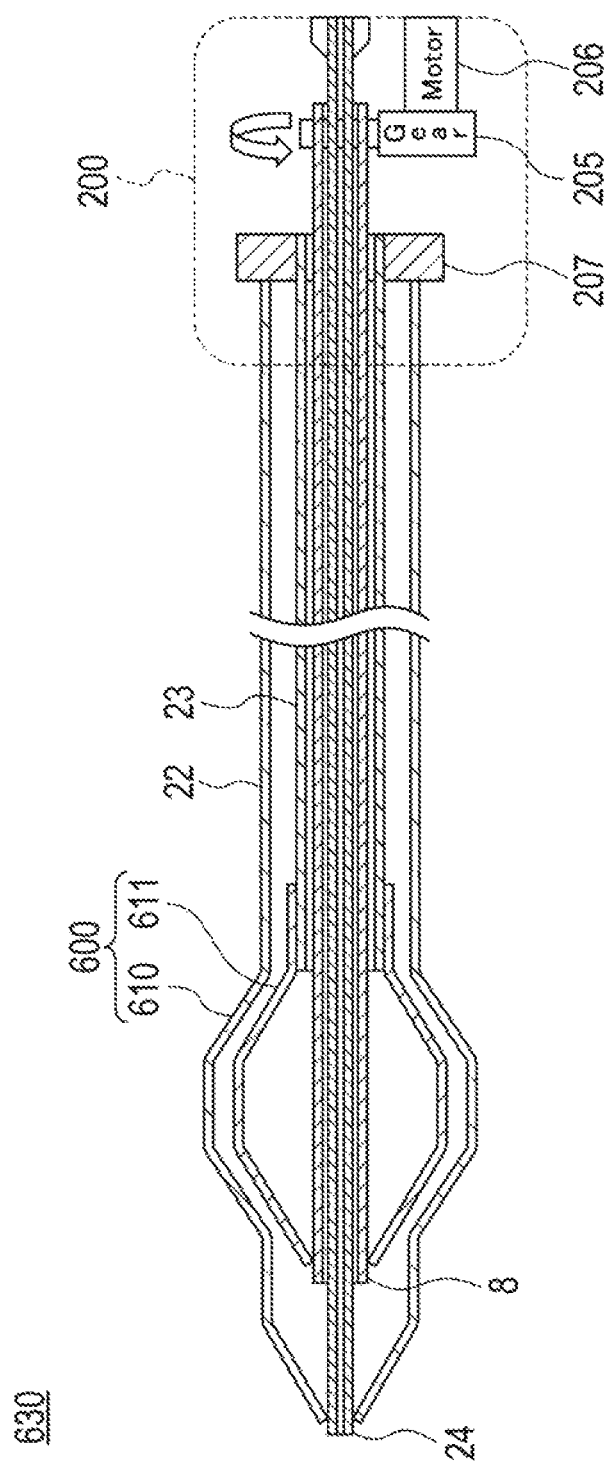
FIG. 24 is a schematic view depicting a modification to the catheter system depicted in FIG. 19.

FIG. 19 is a lateral view depicting a catheter system 1" according to the present embodiment, FIG. 20 is a lateral view of a removing member 600 of a removing device 4" depicted in FIG. 19, and FIG. 21 is a perspective view of the removing member 600 depicted in FIG. 20. FIG. 22A is a sectional view of the proximal side of the catheter system 1" depicted in FIG. 19, and FIG. 22B is a perspective view of FIG. 22A. FIGS. 23A to 23D are diagrammatic views when the removing member 600 acts at the stenosis 400. FIG. 24 is a lateral view of a catheter system 630 which is a modification to the catheter system 1" depicted in FIG. 19.

As depicted in FIG. 19, the catheter system 1" includes an outer catheter 2, a hub 3 provided at a proximal end portion of the outer catheter 2, the removing device 4" fitted in the outer catheter 2 for rotation around an axis and for movement in an axial direction with respect to the outer catheter 2, and the removing member 600 (expandable member) disposed at the distal side or distal end of the removing device 4" and configured to drill and remove an occluding substance which constricts or occludes a vascular lumen. Further, the occluding substance includes not only a substance which occludes a vascular lumen but also various substances which constrict the lumen even if they do not fully occlude the lumen. In particular, examples of the occluding substances include thrombi, fatty streaks, plaques, calcified lesions, intimal hypertrophy of a vessel, arteriosclerosis layers and so forth.

As depicted in FIGS. 20 and 21, the removing member 600 for removing an occluding substance generated in a blood vessel is fixed to a distal end portion of the removing device 4".

The removing member 600 is configured such that it can be deformed, when the outer catheter 2 is operated so as to move in directions indicated by a double-side arrow mark in FIG. 19, between a state in which it is accommodated in the outer catheter 2 and has a reduced diameter and an expanded state in which the removing member 600 projects from a distal end opening 2a of the outer catheter 2 and is expanded in a radial direction by the elastic restoring force of itself as depicted in FIGS. 20 and 21. The removing member 600 is shaped such that it exhibits the expanded state when it is in a natural state (state in which it is not acted upon by any external force). When an occluding substance is to be removed by the removing member 600, the removing member 600 projects from the distal end opening 2a of the outer catheter 2, and treatment for removing the occluding substance is performed in the expanded state of the removing member 600.

The removing member 600 in the expanded state is described below.

As depicted in FIGS. 20 and 21, the removing member 600 is configured from an expandable outer side member 610 continuing to or extending between a distal end part 6 and a proximal end part 7, and an expandable inner side member 611 continuing to or extending between a distal end part and a proximal end part (not depicted) and disposed in the inside of the outer side member 610. The outer side member 610 is configured from four narrow struts 610a each in the form of a thin board portion. In the internal space of the outer side member 610 and the inner side member 611, a drive shaft 8 extends which has a guide wire lumen which is open from the distal end to the proximal end of the removing device 4" and into which a guide wire can be inserted. The distal end part 6 is fixed to the drive shaft 8 through the distal end part of the inner side member 611. The proximal end part 7 is fixed to the proximal end part of the inner side member 611, and the proximal end part of the inner side member 611 is disposed for sliding movement with respect to the drive shaft 8. Consequently, when the removing member 600 is projected from the distal end opening 2a of the outer catheter 2, the removing member 600 starts self-expansion and simultaneously the proximal end part of the inner side member 611 slidably moves on the drive shaft 8 to the distal side or toward the distal direction to allow the removing member 600 to be placed into an expanded state. Further, a rotational force is transmitted from the proximal side or proximal end of the removing device 4" to rotate the drive shaft 8. Consequently, the outer side member 610 continuing to the distal end part 6 fixed to the drive shaft 8 and the inner side member 611 continuing to the distal end part of the inner side member 611 are rotated.

As depicted in FIGS. 20 and 21, the struts 610a of the outer side member 610 are disposed in a displaced relationship by 90 degrees from each other in the circumferential direction. The struts 610a are fabricated by forming four cuts on one metal pipe and memorizing the shape in the expanded state. That is, the shape of the struts 610 is fixed by virtue of the struts being made of a shape-memory alloy. Preferably, the struts 610a are subject to an atraumatic process so as not to damage a contacting location in the body when they are rotated. By the configuration described above, it is possible to remove only a projecting lesion without damaging the stenosis 400 by rotation of the outer side member 610. An example of the atraumatic process includes a process to form a side face as a curved face. Further, struts 611a of the inner side member 611 are fabricated by forming six spiral cuts on one metal pipe and memorizing the shape in the expanded state. By the configuration just described, when the inner side member 611 is placed into the expanded state, the angle of each strut 611a (orientation of a side face of the thin board portion) varies, and removal of an occluding substance using the side face of the strut 611a is allowed. Accordingly, each of the struts 611a of the inner side member 611 is configured as a spiral thin board portion, and, when the inner side member 611 is placed into a reduced diameter state, the struts 611a are configured as a single metal pipe.

As a constituent material of the outer side member 610 and the inner side member 611, for example, it is preferable to use a shape-memory alloy or the like. Examples of the shape-memory alloy include Ni—Ti-based alloys such as Ni—Ti and Ni—Ti—Cu, Cu-based alloys such as Cu—Al—Mn and Cu—Al—Ni, Fe-based alloys such as Fe—Mn—Si, Au—Cd, Ag—Cd-based alloys, ferromagnetic shape memory alloys such as Ni—Mn—Ga and Fe—Pd and so forth.

An example of a method of use of the catheter system 1" is now described. When treatment for removing an occluding substance in a blood vessel is to be performed, the removing device 4" having the removing member 600 disposed at the distal end of the removing device 4" is inserted in advance into the outer catheter 2, and the removing member 600 is accommodated inside the outer catheter 2 at the distal side of the outer catheter 2 in a state in which the outer diameter of the removing member 600 is reduced. The removing device 4" and the outer catheter 2 are inserted into a target region in the blood vessel by guiding the removing device 4" and the outer catheter 2 along a guide wire inserted or positioned in the guide wire lumen of the drive shaft 8. The situation at this time is monitored by X-ray contrast or the like.

Then, the removing device 4" disposed in the outer catheter 2 is pushed to move to the peripheral side of the blood vessel (in the forward direction) in a state in which the outer catheter 2 is fixed at the proximal side of the outer catheter 2 so as not to move. Consequently, the removing member 600 projects distally from or distally beyond the distal end opening 2a of the outer catheter 2 and is expanded in a radial direction so as to be placed into an expanded state by its own elastic restoring force as depicted in FIGS. 20 and 21. Alternatively, the removing member 600 may be positioned to project distally beyond the distal end opening 2a of the outer catheter 2 by pulling back the outer catheter 2 in a state in which the removing device 4" is fixed at the hand side or proximal end.

Then, the removing member 600 is brought into contact with the occluding place (stenosis 400) in the blood vessel and the removing member 600 is rotated around the drive shaft 8. Consequently, the removing member 600 is rotated around the drive shaft 8, and the struts 611a of the inner side member 611 remove the occluding substance which forms the stenosis or occlusion. Depending upon the disease state of the blood vessel, a method of pressing the removing member 600 stronger against the lesion affected area to perform treatment is sometimes effective. In this case, a reinforcing tube 101' (refer to FIGS. 22A and 22B) is slidably (axially) moved to the distal side or distal end along the drive shaft 8 to push in (forwardly push) the proximal end part 7 of the outer side member 610 and the proximal end part of the inner side member 611 thereby to control the outer diameter of the removing member 600. Consequently, the operator can perform selective treatment while obtaining a sense at the hand-operated side or proximal end.

The action of a motor unit 100' for driving the removing member 600 is now described with reference to the diagrammatic views depicted in FIGS. 22A and 22B. The motor unit 100' is a box-type unit device having an internal space 105'. The distal end portion of the motor unit 100' has a lumen into which the drive shaft 8 is inserted or positioned, and has a reinforcing tube 101' whose proximal end portion is fixed to the motor unit 100'. The drive shaft 8 is inserted into or positioned inside the motor unit 100' in a state in which the drive shaft 8 is fitted in a lumen of the reinforcing tube 101'. As depicted in FIGS. 20, 21, 22(A) and 22(B), the reinforcing tube 101' distally extends to a location in the proximity of the proximal end of the removing member 600.

Here, as depicted in FIGS. 22A and 22B, the proximal end of the drive shaft 8 is connected to a predetermined connector 102', and the connector 102' is connected to a motor driving unit. The motor driving unit transmits the rotational force to the drive shaft 8. Preferably, the number of rotations of the motor driving unit (rotational speed of the motor driving unit during operation to perform the disclosed methods) is 1,000 rpm to 200,000 rpm.

The drive shaft 8 is disposed in a state in which the outer surface of the drive shaft 8 has a small clearance from, or is in contact with, the inner surface of the reinforcing tube 101'. In the present embodiment, since the drive shaft 8 is configured from a super elastic alloy such as Ni—Ti having a relatively high kink resistance and the reinforcing tube 101' is configured from a material having a comparatively high rigidity (i.e., the reinforcing tube 101' has a higher rigidity, and is more rigid, than the drive shaft 8), vibration or wobbling generated by the driving force applied to the drive shaft 8 from the motor driving unit can be absorbed.

Especially, where the removing device 4" is disposed on a traveling path having many curves such as a blood vessel, the influence of vibration or wobbling generated by the driving force applied from the motor driving unit is significant. However, the influence can be suppressed by the reinforcing tube 101', and the driving force can be efficiently transmitted to the distal side.

Further, while the size of the reinforcing tube 101' is not specifically limited, for example, it is preferable to set the outer diameter, inner diameter and length in the axial direction to approximately 1.5 mm to 3.5 mm, approximately 1.3 mm to 3.3 mm and approximately 30 cm to 150 cm, respectively. The outer diameter of the drive shaft 8 is set so as to slidably contact with the inner surface of the reinforcing tube 101'.

The reinforcing tube 101' has a cylindrical shape having a fixed or constant outer diameter from a proximal end portion of the reinforcing tube 101' to a distal end portion of the reinforcing tube 101'. The reinforcing tube 101' has a three-layer structure configured from an inner layer, an intermediate layer provided on the outer circumference of the inner layer and an outer layer provided on the outer circumference of the intermediate layer, and has flexibility such that the reinforcing tube 101' can be bent freely along the curves of a blood vessel upon insertion into the blood vessel. Examples of the materials which can be used to fabricate the components configuring the reinforcing tube 101' include materials similar to those of the above-described reinforcing tube 101 (refer to FIGS. 4A and 4B).

The action of the catheter system 1" is now described with reference to diagrammatic views of a lesion depicted in FIGS. 23A to 23D. When the removing device 4" comes to a lesion affected area, the distal side or distal end of the removing member 600 is brought into contact with the stenosis 400 as depicted in FIG. 23A. Here, since the removing member 600 performs rotational movement (i.e., rotates) by driving or operating the motor driving unit, removal of the stenosis 400 can be performed by the struts 611a of the inner side member 611. Further, since the removing member 600 here is shaped so as to self-expand in a radial direction, a pressing force equal to or higher than a predetermined level can be applied usually to the stenosis 400. Therefore, treatment which does not rely upon the position, size, hardness and so forth of the stenosis 400 can be carried out. Further, the removing member 600 can be inserted into the inside of the stenosis 400 as depicted in FIG. 23B so that an outermost diameter portion of the removing member 600 contacts the stenosis 400, and the stenosis 400 can be removed by driving or operating the motor driving unit. Further, positioning the removing member 600 at the peripheral side or distal side in the blood vessel with respect to the stenosis 400 and operating the removing device 600 so as to be pulled back to the proximal side or in the proximal direction as depicted in FIG. 23C causes the proximal side or proximal end of the removing member 600 to contact the stenosis 400. Then, by driving or operating the motor driving unit in this state, the stenosis 400 can be removed similarly. Also it is possible to dispose the removing member 600 in a state in which the stenosis 400 is sandwiched between the struts 610a of the outer side member 610 and the struts 611a of the inner side member 611 as depicted in FIG. 23D. In this state, the stenosis 400 can be cut by driving or operating the motor driving unit.

As described above, with the catheter system 1", by inserting the removing member 600 to a location in the proximity of the stenosis 400 of the blood vessel and performing an operation for moving the removing member 600 in a direction toward the stenosis 400 while the motor driving unit is driven in a state in which the removing member 600 abuts an occluding substance which constricts the blood vessel, the occluding substance of the stenosis 400 can be gradually drilled and removed by the struts 611a of the inner side member 611. Therefore, the occluding substance can be drilled and removed easily, quickly and with certainty.

Consequently, since the occluding substance of the stenosis 400 can be removed, the blood vessel is placed into a communication state and blood flow can be secured, and a route for various devices to be used at succeeding treatment steps can be formed. Consequently, the succeeding treatment steps (expansion treatment by a balloon catheter, expansion by a stent or the like, and so forth) can be performed readily.

Further, since the outer side member 610 of the removing member 600 according to the present embodiment is configured from an atraumatic member, also by the above-described rotational operation, a projecting occluding substance can be scraped off by the inner side member 611 without damaging a normal blood vessel wall. Therefore, the blood vessel wall after treatment can be kept in a clean state. Further, the outer side member 610 includes the plurality of struts 610a whose side face is processed as a curved face and is configured from a shape-memory alloy by which the shape of the struts in an expanded state is memorized. Therefore, the outer side member 610 having both of the atraumatic characteristic and the self-expansion characteristic can be provided. Furthermore, the inner side member 611 includes the plurality of struts 611a extending spirally and is configured from a shape-memory alloy by which the shape thereof in an expanded state is memorized. Therefore, the inner side member 611 having both of the traumatic characteristic and the self-expansion characteristic can be provided.

The catheter system 1" further includes the drive shaft 8 fitted in the internal space of the inner side member 611 and the internal space of the outer side member 610, and a distal end portion (distal end part) of the inner side member 611 is fixed to the drive shaft 8 and a proximal end portion (proximal end part) of the inner side member 611 is disposed for sliding movement with respect to the drive shaft 8. Further, the distal end portion (distal end part) 6 of the outer side member 610 is fixed to the distal end portion of the inner side member 611 and the proximal end portion (proximal end part) 7 of the outer side member 610 is fixed to the proximal end portion of the inner side member 611. Since the catheter system 1" is configured in such a manner as described above, performing an operation to cause the removing member 600 (the inner side member 611 and the outer side member 610) to project from the distal end opening 2a of the outer catheter 2 results in the proximal end portion of the inner side member 611 slidably or axially moving on the drive shaft 8 to the distal side or in the distal direction, and the inner side member 611 and the outer side member 610 start self-expansion until they are placed into an expanded state. Since the inner side member 611 and the outer side member 610 can be expanded by a simple operation, a technique can be performed smoothly.

Further, while it is described in the present embodiment that the removing member 600 is placed into an expanded state by self-expansion, the removing member 600 may be configured such that it can be placed into an expanded state by a manual operation. In this case, the reinforcing tube 101' is slidably moved in a direction toward the distal end with respect to the drive shaft 8 such that the proximal end part 7 of the outer side member 610 and the proximal end part of the inner side member 611 are pushed in by the distal end of the reinforcing tube 101' thereby to perform expansion of the outer side member 610 and the inner side member 611. In this case, the operator can adjust the contacting state of the removing member 600 with the stenosis 400 in accordance with the sense at the hand side.

Now, a modification to the catheter system 1" according to the above-described embodiment is explained. Like elements to those in the aforementioned embodiment are denoted by like reference symbols and a detailed description of such features is not repeated.

FIG. 24 is a sectional view depicting a catheter system 630 according to the modification.

As depicted in FIG. 24, the catheter system 630 according to the modification includes a removing member 600 configured from an outer side member 610 and an inner side member 611, a drive shaft 8 connected to a motor driving unit 206 disposed in a motor unit 200, a guide wire lumen (shaft) 24 inserted in a lumen of the drive shaft 8, an inner tube 23 in the inside of which the drive shaft 8 is inserted and whose proximal side and distal end are connected to a bearing 207 in the motor unit 200 and the inner side member 611, respectively, and an outer tube 22 in the inside of which the inner tube 23 is inserted and whose proximal side and distal end are connected to the bearing 207 and the outer side member 610, respectively. The distal end of the outer side member 610 is connected to the guide wire lumen 24.

The inner side member 611 and the outer side member 610 can be configured similarly to those in the above-described embodiment.

The action of the catheter system 630 is now described. First, the bearing 207 is moved in the direction toward the distal end to expand the inner side member 611 and the outer side member 610 so that they are placed into an expanded state. Then, the motor driving unit 206 in the motor unit 200 is driven, and the drive shaft 8 connected to the motor driving unit 206 through a predetermined gear 205 is rotated. Consequently, the inner side member 611 connected to the drive shaft 8 rotates and also the inner tube 23 connected to the inner side member 611 rotates. The rotation of the inner tube 23 is transmitted to the proximal side, and the rotational force is absorbed by rotation of the bearing 207.

In the present modification, since rotation transmitted by the motor driving unit 206 is absorbed by the bearing 207 through the proximal side, it is possible to allow only the inner side member 611 to rotate. Especially, since the guide wire lumen 24 is not rotated, treatment can be performed without moving the distal end position of a guide wire fitted in the guide wire lumen 24. Further, since also the outer side member 610 is not rotated, treatment can be performed safely without damaging a blood vessel wall in the proximity of a lesion affected area.

To the catheter system according to the present embodiment, for example, a filter for covering the removing member 600 can be added. Further, when the removing member 600 is used, the filter device 300 may be used (refer to FIG. 7). Consequently, fine debris or the like broken-off or separated by the removing member 600 flow to the peripheral side of the blood vessel.

While the catheter system has been described on the basis of the embodiments and modifications depicted in the drawings, the present disclosure is not limited to this, and the configuration of any component can be replaced by an other configurations having similar functions.

Further, the region (location) from which an occluding substance is to be removed by the catheter system is not limited to a blood vessel, and, as a different region, for example, a bile duct, a urethra and so forth are listed. Further, as an occluding substance, for example, a thrombus, a fatty streak, a plaque, an arteriosclerosis layer, a calculus and so forth are listed.

The detailed description above describes embodiments of a medical device and a method for treating a stenosis or an occluded portion of a living body representing examples of the medical device and method disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device positionable in a living body lumen for removing a stenosis of the living body lumen, comprising:
   a drive shaft possessing distal and proximal portions, and configured to be rotatably driven by an operation at the proximal portion of the drive shaft, the drive shaft possessing an outer surface, the drive shaft including a removing member disposed at the distal portion of the drive shaft;
   an outer catheter positionable in the living body lumen and configured to accommodate the removing member while the outer catheter is positioned in the living body lumen, the removing member being a self-expanding removing member that is configured to self-expand radially outwardly when the removing member in a contracted state and accommodated in the outer catheter is moved to outside the outer catheter so that the self-expanding removing member radially outwardly self-expands to an expanded state;
   the removing member being comprised of a plurality of elongated struts configured to contact the stenosis during operation of the medical device, each of the elongated struts possessing a distal-most end fixed directly to a distal end piece and a proximal-most end fixed directly to a proximal end piece so that the elongated struts extend from the distal end piece to the proximal end piece, the distal end piece being located distal of the proximal end piece, the proximal end piece to which the proximal-most ends of the elongated struts are directly fixed possessing a proximal-most end, the distal end piece being fixed to the drive shaft, the proximal end piece being mounted on the drive shaft so that the proximal end piece surrounds the drive shaft, the elongated struts being positioned outwardly of the drive shaft;
   a housing configured to accommodate the proximal portion of the drive shaft;
   a tube in which the drive shaft is positioned, the tube possessing a proximal end, a distal end and an inner surface;
   the proximal end of the tube being fixed to the housing;
   the distal-most end of the tube being a positioned proximal of the proximal-most end of the proximal end piece to which the proximal-most ends of the elongated struts are directly fixed; and
   the inner surface of the tube and the outer surface of the drive shaft being slidable relative to one another.

2. The medical device according to claim 1, further comprising:
   a bearing interlocked with a proximal end of the drive shaft and a distal end of a driving source; and
   wherein the bearing freely rotates only the drive shaft to transmit driving force from the driving source to the drive shaft.

3. The medical device according to claim 1, wherein the struts each include a plurality of protrusions spaced apart along a length of the strut and projecting in a circumferential direction.

4. The medical device according to claim 3, wherein the removing member is rotatable and axially movable while the struts are in contact with the stenosis in the living body lumen to remove the stenosis, wherein the struts each include a plurality of through holes spaced apart along the length of the strut.

5. The medical device according to claim 1, wherein the plurality of elongated struts are circumferentially spaced-apart struts, and further comprising a filter positioned at the distal end part of the removing member to capture parts of the stenosis removed by the struts.

6. The medical device according to claim 1, wherein the distal-most end of the tube is positioned proximal of the proximal-most end of the proximal end piece to which the proximal-most ends of the elongated struts are directly fixed.

7. The medical device according to claim 1, wherein the proximal end piece to which the proximal-most ends of the elongated struts are directly fixed possesses a constant outer diameter along its length.

8. The medical device according to claim 1, wherein the proximal end piece possesses an outer surface, the inner surface of the tube being located radially outwardly of the outer surface of the proximal end piece.

9. The medical device according to claim 1, wherein the proximal end piece possesses an outer surface, the inner surface of the tube and the outer surface of the proximal end piece being separate from one another.

10. The medical device according to claim 1, wherein the tube possesses an outer diameter greater than an outer diameter of the proximal end piece.

11. The medical device according to claim 1, wherein the tube possesses an outer diameter, the outer diameter of a distal end portion of the tube being constant.

12. The medical device according to claim 1, wherein the proximal end piece and the tube are configured so that when the removing member is outside the outer catheter, axial movement of the tube in a distal direction relative to the drive shaft results in distal direction axial movement of the proximal end piece to which the proximal-most ends of the elongated struts are directly fixed in the distal direction.

13. The medical device according to claim 1, wherein the proximal end piece and the tube are configured so that when the removing member is outside the outer catheter, axial movement of the tube relative to the drive shaft results in distal direction axial movement of the proximal end piece to which the proximal-most ends of the elongated struts are directly fixed in the distal direction.

14. A medical device positionable in a living body lumen for removing a stenosis of the living body lumen, comprising:
   a drive shaft possessing distal and proximal portions, and configured to be driven by an operation at the proximal portion of the drive shaft, the drive shaft possessing an outer surface, the drive shaft including a removing member disposed at the distal portion of the drive shaft;
   an outer catheter positionable in the living body lumen and configured to accommodate the removing member while the outer catheter is positioned in the living body lumen, the removing member being deformable to change between a contracted state in which the removing member is radially inwardly contracted while the removing member is accommodated in the outer catheter, and an expanded state in which the removing member is radially outwardly expanded while the removing member is located outside the outer catheter so that the removing member in the expanded state is positioned in the living body lumen;
a housing configured to accommodate the proximal portion of the drive shaft;
a tube in which the drive shaft is positioned, the tube possessing a proximal end and an inner surface;
the proximal end of the tube being fixed to the housing;
the inner surface of the tube and the outer surface of the drive shaft being slidable relative to one another; and
wherein the drive shaft includes a projection, wherein the housing includes a spiral-shaped groove in which the projection is positioned so that the spiral-shaped groove guides the projection, and wherein the projection positioned in the spiral-shaped groove is configured to cause the drive shaft to rotate when the drive shaft is pushed in a distal direction from the proximal portion of the drive shaft.

15. The medical device according to claim 14, wherein the removing member includes a plurality of elongated struts that each possess a proximal end and a distal end.

16. The medical device according to claim 15, wherein each of the elongated struts includes a plurality of spaced apart protrusions that project outwardly away from the strut.

17. The medical device according to claim 15, wherein the distal end of each of the plurality of elongated struts is fixed relative to the drive shaft, and the proximal end of each of the plurality of elongated struts is axially movable relative to the drive shaft.

18. The medical device according to claim 15, wherein the proximal end of each of the plurality of elongated struts is fixed relative to the drive shaft, and the distal end of each of the plurality of elongated struts is axially movable relative to the drive shaft.

19. The medical device according to claim 15, wherein the distal end of each of the plurality of elongated struts and the proximal end of each of the plurality of elongated struts are fixed relative to the drive shaft to rotate together with the drive shaft.

20. The medical device according to claim 14, wherein a distal end of each of the elongated struts is connected to a distal end piece mounted on the drive shaft, and a proximal end of each of the elongated struts is connected to a proximal end piece mounted on the drive shaft.

21. The medical device according to claim 20, wherein the distal end of each of the elongated struts is fixed directly to the distal end piece, and the proximal end of each of the elongated struts is fixed directly to the proximal end piece.

22. A medical device positionable in a living body lumen for removing a stenosis of the living body lumen, comprising:
a drive shaft possessing a proximal end portion configured to be connected to a motor to rotate the drive shaft during operation of the medical device, the drive shaft also possessing a distal end portion and an outer surface;
an outer catheter positionable in the living body lumen;
a removing member at the distal end portion of the drive shaft, the removing member including a plurality of circumferentially spaced apart and non-woven self-expanding struts that self-expand radially outwardly when the struts in a contracted state and accommodated in the outer catheter are moved to outside the outer catheter so that the self-expanding struts radially outwardly self-expand to an expanded state;
the plurality of struts each possessing a distal-most end connected to a distal end piece and a proximal-most end connected to a proximal end piece so that the plurality of struts extend from the distal end piece to the proximal end piece, the plurality of struts surrounding a space through which passes the drive shaft, the drive shaft axially overlapping both the distal end piece and the proximal end piece, the distal end piece being fixed to the drive shaft to rotate together with the drive shaft, the proximal end piece being mounted on the drive shaft so that the proximal end piece surrounds the drive shaft, the proximal end piece being slidable on and relative to the drive shaft;
each of the struts including a plurality of spaced apart protrusions that project outwardly away from the strut;
a housing configured to accommodate the proximal end portion of the drive shaft;
a tube in which the drive shaft is positioned, the tube possessing a proximal end, a distal end and an inner surface;
the proximal end of the tube being fixed to the housing;
the distal end of the tube and at least a part of the proximal end piece axially overlapping one another, and
the inner surface of the tube and the outer surface of the drive shaft being slidable relative to one another.

23. A medical device positionable in a living body lumen for removing a stenosis of the living body lumen, comprising:
a drive shaft possessing distal and proximal portions, and configured to be rotatably driven by an operation at the proximal portion of the drive shaft, the drive shaft possessing an outer surface, the drive shaft including a removing member disposed at the distal portion of the drive shaft;
an outer catheter positionable in the living body lumen and configured to accommodate the removing member while the outer catheter is positioned in the living body lumen, the removing member being a self-expanding removing member that is configured to self-expand radially outwardly when the removing member in a contracted state and accommodated in the outer catheter is moved to outside the outer catheter so that the self-expanding removing member radially outwardly self-expands to an expanded state;
the removing member being comprised of a plurality of elongated struts configured to contact the stenosis during operation of the medical device, each of the elongated struts possessing a distal-most end fixed directly to a distal end piece and a proximal-most end fixed directly to a proximal end piece so that the elongated struts extend from the distal end piece to the proximal end piece, the distal end piece being located distal of the proximal end piece, the proximal end piece to which the proximal-most ends of the elongated struts are directly fixed possessing a proximal-most end, the distal end piece being fixed to the drive shaft, the proximal end piece being mounted on the drive shaft so that the proximal end piece surrounds the drive shaft, the elongated struts being positioned outwardly of the drive shaft;
a housing configured to accommodate the proximal portion of the drive shaft;

a tube in which the drive shaft is positioned, the tube possessing a proximal end, a distal end and an inner surface;

the proximal end of the tube being fixed to the housing;

the tube being positioned inside the outer catheter when the removing member is accommodated in the outer catheter and being axially movable in a distal direction relative to the outer catheter so that a distal portion of the tube is moved from a position inside the outer catheter to a position outside the outer catheter and distal of a distal end of the outer catheter when the removing member is moved to outside the outer catheter; and the inner surface of the tube and the outer surface of the drive shaft being slidable relative to one another.

24. The medical device according to claim 23, wherein the removing member is connected to a distal portion of the tube.

25. The medical device according to claim 23, wherein the distal-most end of the tube is positioned proximal of the proximal-most end of the proximal end piece to which the proximal-most ends of the elongated struts are directly fixed.

26. The medical device according to claim 23, wherein the tube and the drive shaft each exhibit rigidity.

* * * * *